US007273719B2

(12) United States Patent
Roth et al.

(10) Patent No.: US 7,273,719 B2
(45) Date of Patent: *Sep. 25, 2007

(54) **TEST MEDIA FOR QUANTITATIVE OR QUALITATIVE IDENTIFICATION AND DIFFERENTIATION OF GENERAL COLIFORMS, *E COLI*, *AEROMONAS* SPP AND *SALMONELLA* SPP MATERIALS IN A TEST SAMPLE**

(75) Inventors: Geoffrey N Roth, Goshen, IN (US); Jonathan N Roth, Goshen, IN (US)

(73) Assignee: Micrology Laboratories, LLC, Goshen, IN (US)

( * ) Notice: Subject to any disclaimer, the term of this patent is extended or adjusted under 35 U.S.C. 154(b) by 379 days.

This patent is subject to a terminal disclaimer.

(21) Appl. No.: 10/867,393

(22) Filed: Jun. 14, 2004

(65) Prior Publication Data

US 2004/0235087 A1    Nov. 25, 2004

Related U.S. Application Data

(63) Continuation-in-part of application No. 10/040,791, filed on Jan. 7, 2002, now Pat. No. 6,787,332, which is a continuation of application No. 09/357,606, filed on Jul. 20, 1999, now Pat. No. 6,350,588.

(51) Int. Cl.
*C12Q 1/04*    (2006.01)
(52) U.S. Cl. .......................................... 435/34; 435/38
(58) Field of Classification Search .................. 435/34, 435/38, 7.32, 7.35, 252.4, 252.8
See application file for complete search history.

(56) References Cited

U.S. PATENT DOCUMENTS

| | | | |
|---|---|---|---|
| 4,308,348 A | 12/1981 | Monget | |
| 5,093,239 A | 3/1992 | Belly et al. | |
| 5,210,022 A | 5/1993 | Roth et al. | |
| 5,358,854 A | 10/1994 | Ferguson | |
| 5,364,767 A | 11/1994 | Flowers et al. | |
| 5,393,662 A | 2/1995 | Roth et al. | |
| 5,443,963 A | 8/1995 | Lund | |
| 5,541,082 A | 7/1996 | Botchner | |
| 5,643,743 A | 7/1997 | Chang et al. | |
| 5,726,031 A | 3/1998 | Roth et al. | |
| 5,786,167 A | 7/1998 | Tuompo et al. | |
| 5,837,482 A | 11/1998 | Mach et al. | |
| 5,888,760 A | 3/1999 | Godsey et al. | |
| 5,962,251 A | 10/1999 | Rambach | |
| 5,989,892 A | 11/1999 | Nishimaki et al. | |
| 6,008,008 A | 12/1999 | James et al. | |
| 6,350,588 B1* | 2/2002 | Roth et al. | 435/34 |
| 6,787,332 B2* | 9/2004 | Roth et al. | 435/34 |

FOREIGN PATENT DOCUMENTS

| | | |
|---|---|---|
| EP | 0122028 A1 | 10/1984 |
| WO | WO 96/40980 | 12/1996 |
| WO | WO 98/55644 | 12/1998 |

OTHER PUBLICATIONS

Van Poucke S. O. et al. Rapid Detection of Fluorescent and Chemiluminescent Total Coliforms and *E. coli* on Membrane Filters. J of Microbiological Methods. 2000 vol. 42, pp. 233-244.*
Borrego J. et al., Microbiological Quality of Natural Waters, Microbiologia Sem 13, 1997, 413-426.
Brenner, K.P et al., New Medium for the Simultaneous Detection of Total Coliforms and *Escherichia coli* in Water, Applied & Environ. Microbiol., Nov. 1993, pp. 3534-3544.
E-Colite- Single Step Presence/Absence of Coliforms and/or *E.coli*, Charm Sciences, Inc., 1996, 2 pages.
Dalet, F. et al, Evaluation of a new agar in Uricult-Trio for rapid detection of *Escherichia coli* in urine, J. Clin Microbiol., May 1995, pp. 1395-1398, 33(5), Abstract Only.
Evans, T.M. et al., Failure of the Most-Probable-Number Technique to Detect Coliforms in Drinking et al., Applied & Environ. Microbiol., Jan. 1981, p. 130-138.
Grant, M.A., A New Membrane Filtration Medium for Simultaneous Detectioin and Enumeration et al., Applied & Environ. Microbiol., Sep. 1997, pp. 3526-3530.
James, A.L. et al, Detection of Specific Bacterial Enzymes by High et al. (Part I), Zentralbl Bakteriol Mikrobiol Hyg A267 (2), Dec. 1987, pp. 188-193, (Abstract Only).
James, A.L. et al., Detection of Specific Bacterial Enzymes by High et al. (Part II), Zbl. Bakt. Hyg A 267, 1988, pp. 316-321.
James, A.L. et al., Note: cyclohexenoesculetin-beta-D-glucoside: a new substrate for the detection et al., J. Appl. Microbiol., Apr. 1997, 82(4), pp. 532-536 (Abstract Only).
James A.L. et al., Evaluation of Cyclohexenoesculetin-B-D-Galactoside and 8-Hydroxyquinoline-B-D-Galactoside et al., App. & Environ. Microbiol., Oct. 1996, pp. 3868-3870.
Johnson, J.R., Shigella and *E. coli*, Association ASM Letter Editor, undated, 1 page.

(Continued)

*Primary Examiner*—Ralph Gitomer
(74) *Attorney, Agent, or Firm*—Baker & Daniels LLP

(57) ABSTRACT

A test medium and method for detecting, quantifying, identifying and differentiating up to four (4) separate biological materials in a test sample. A test medium is disclosed which allows quantifying and differentiating under ambient light aggregates of biological entities producing specific enzymes, which might include general coliforms, *E. coli*, *Aeromonas*, and *Salmonella* in a single test medium. A new class of nonchromogenic substrates is disclosed which produce a substantially black, non-diffusible precipitate. This precipitate is not subject to interference from other chromogenic substrates present in the test medium. In one embodiment, the substrates are selected such that *E. coli* colonies present in the test medium show as substantially black, general coliforms colonies show in the test medium as a blue-violet color, *Aeromonas* colonies present in the test medium show as a generally red-pink color, and *Salmonella* colonies show as a generally teal-green color. Other microorganisms and color possibilities for detection and quantification thereof are also disclosed. An inhibitor and method for making a test medium incorporating the inhibitor are disclosed.

10 Claims, No Drawings

OTHER PUBLICATIONS

Kampfer, P. et al., Fluorogenic Substrates for Differentiation of Gram-Negative Nonfermentative and Oxidase- et al., Journ. of Clinical Microbiol., Jun. 1992, pp. 1402-1406.

Kampfer, P. et al., Glycosidase Profiles of Members of the Family Enterobacteriaceae, Journ. of Clinical Microbiol., Dec. 1991, pp. 2877-2879.

Killian, M. et al., Rapid Diagnosis of Enterbacteriaceae, Acta path. microbiol., scand. Sect. B, 1976, pp. 245-251.

Landre, J.P.B., False-Positive Coliform Reaction Mediated by Aeromonas et al., Letters in Appl. Microbiol., 1998, pp. 352-354.

Larinkari U. et al., Evaluation of a new dipslide with a selective medium for the et al., Eur J Clin Microbiol Infect Dis, Jul. 1995, pp. 606-609.

Legnani, P. et al., The occurence of *Aeromonas* species in drinking water et al., Journal of App. Microbiol., 1998, pp. 271-276, vol. 85.

Lupo, L. et al., The effect of oxidase positive bacteria on total coliform density estimates, Health lab Sci, Apr. 1977, pp. 117-121, (Abstract Only).

Manafi, M., Fluorogenic and chromogenic enzyme substrates in culture media and identification tests, International Journ. of food Microbiol., 1996, pp. 45-58.

Manafi, M., et al., Fluorogenic and Chromogenic Substrates Used in Bacterial Diagnostics, Microbiol. Reviews, Sep. 1991, pp. 335-348.

Manafi, M. et al., A new plate medium for rapid presumptive identification et al., International Journ. of Food Microbiol., 1991, pp. 127-134.

Mates, A. et al., Membrane filtration differntiation of *E. coli* from coliforms in the examination of water, Journ. of Appl. Bacteriology, 1989, pp. 343-346, vol. 67.

McDaniels, A.E., et al., Confirmational Identification of *Escherichia coli*, a Comparison et al., Appl. & Environ. Microbiol., Sep. 1996, pp. 3350-3354.

Packer, P.J., et al., Comparison of Selective Agars for the Isolation and Identification et al., Letters in Appl. Microbiol., 1995, pp. 303-307, vol. 20.

Perry, J.D. et al., ABC Medium, a new chromogenic agar for selective isolation of *Salmonella* spp., Journ. of Clinical Microbiol., Mar. 1999, pp. 766-768.

Pettibone, G.W., Population dynamics of *Aeromonas* spp. in an urban river et al., Appl. Microbiol., 1998, pp. 723-730, vol. 85.

Pocsi, I. et al., Comparison of several new chromogenic galactosides as substrates for various B-D-galactosidases, Biochimica et aBiophysica Acta., 1993, p. 54-60, V. 1163.

Quality of Water—Quality of Life, Centr. eur. J. Pub. hlth 7, 1999, p. 216-220, No. 4.

Ramteke, P.W., et al., Incidence of *Aeromonas* in Total Coliform Test, Indian J. Microbiol., Jun. 1992, pp. 193-196, vol. 32(2).

Restaino, L., Accentuate the Postive, Food Quality, Nov./Dec. 1996, pp. 67-69.

Sartory, D., A Simple Membrane Enumberation Medium for Coliforms and *E. coli* utilizing et al., Proceedings Water Quality Technology Conference, 1992, p. 1661-1673.

Sartory, D., et al. A medium detecting B-glucuronidase for the simultaneous membrane filtration enumeration, Letters in Appl. Microbiol., 1992, p. 273-276.

Seidler, Ramon J., Potential Pathogens in the Environment: Cultural Reactions and Nucleic et al., Appl. Microbiol., Jun. 1975, p. 819-825.

\* cited by examiner

TEST MEDIA FOR QUANTITATIVE OR QUALITATIVE IDENTIFICATION AND DIFFERENTIATION OF GENERAL COLIFORMS, *E COLI*, *AEROMONAS* SPP AND *SALMONELLA* SPP MATERIALS IN A TEST SAMPLE

CLAIM OF PRIORITY

This Application is a continuation-in-part of U.S. application Ser. No. 10/040,791 filed on Jan. 7, 2002 and issued as U.S. Pat. No. 6,787,332, which is a continuation of U.S. application Ser. No. 09/357,606 filed on Jul. 20, 1999 and issued as U.S. Pat. No. 6,350,588, all of which are incorporated by reference as if fully rewritten herein.

BACKGROUND OF THE INVENTION

The present invention relates to a test medium and method for the detection, quantification, identification and/or differentiation of biological materials in a sample which may contain a plurality of different biological materials.

Bacteria are the causative factor in many diseases of humans, higher animals and plants, and are commonly transmitted by carriers such as water, beverages, food and other organisms. The testing of these potential carriers of bacteria is of critical importance and generally relies on "indicator organisms." Borrego et al., *Microbiol. Sem.* 13:413-426, (1998). For example, *Escherichia coli* (*E. coli*) is a gram negative member of the family Enterobacteriaceae which is part of the normal intestinal flora of warm blooded animals, and its presence indicates fecal contamination (e.g., raw sewage). Even though most strains of *E. coli* are not the actual cause of disease, their presence is a strong indication of the possible presence of pathogens associated with intestinal disease, such as cholera, dysentery, and hepatitis, among others. Consequently, *E. coli* has become a prime indicator organism for fecal contamination, and as a result, any method which differentiates and identifies *E. coli* from other bacteria is very useful.

Others members of the family Enterobacteriaceae, commonly referred to as "general coliforms," especially the genera *Citrobacter*, *Enterobacter* and *Klebsiella*, are also considered to be significant indicator organisms for the quality of water, beverages and foods. Therefore, tests to identify and differentiate general coliforms from *E. coli* are also very useful. Also, various species of the genus *Aeromonas* have been shown to not only be potential pathogens, but to have a correlation to other indicator organisms (Pettibone et al., *J. Appl. Microbiol.* 85:723-730 (1998)). Current test methods to identify, separate and enumerate *Aeromonas* spp. from the very similar Enterobacteriaceae have been lacking and most of the current methods utilizing enzyme substrates do not separate *Aeromonas* spp. from Enterobacteriaceae due to their almost identical biochemical profiles. Any method that depends upon the identification of general coliforms by means of a β-galactosidase substrate either does not differentiate *Aeromonas* spp. from general coliforms or eliminates *Aeromonas* from the sample by the use of specific inhibitors (antibiotic such as cefsulodin). Brenner et al., *Appl. Envir. Microbio.* 59:3534-44 (1993). They do not differentiate, identify and enumerate *Aeromonas* along with *E. coli* and general coliforms. Landre et al., *Letters Appl. Microbiol.* 26:352-354(1998). Improved test methods to effectively identify, separate and enumerate such bacterial types are needed, and there is a continuing search for faster, more accurate, easier to use and more versatile test methods and apparatus in this area.

Numerous test methods have been utilized to determine, identify and enumerate one or more indicator organisms. Some of these test methods only indicate the presence or absence of the microorganism, while others also attempt to quantify one or more of the particular organisms in the test sample. For example, a qualitative test referred to as the Presence/Absence (or P/A) test, may be utilized to determine the presence or absence of coliforms and *E. coli* in a test sample. A test medium including the β-galactosidase substrate O-nitrophenyl-β-D-galactopyranoside (ONPG), and the β-glucuronidase substrate 4-methyl-umbrelliferyl-β-D-glucuronide (MUG), is inoculated with the test sample. To differentiate the general coliforms from *E. coli*, this test relies on the fact that generally all coliforms produce β-galactosidase, whereas only *E. coli* also produces β-glucuronidase in addition to β-galactosidase. If any coliforms are present (including *E. coli*), the broth medium turns a yellow color due to the activity of the galactosidase enzyme on the ONPG material, causing the release of a diffusible yellow pigment. If *E. coli* is present, the broth medium will demonstrate a blue fluorescence when irradiated with ultraviolet rays, due to the breakdown of the MUG reagent with the release of the fluorogenic dye caused by the production of the glucuronidase enzyme. These reactions are very specific, and allow the presence of both coliforms in general, as well as *E. coli* to be identified in a single sample. A disadvantage of this test is that it is not directly quantitative for either bacterial type, since both reagents produce diffusible pigments. A second disadvantage is that there may a false positive coliform reaction if *Aeromonas* spp. are present in the test sample. This has been shown to be possible even when there are inhibitors present to supposedly prevent this from occurring (Landre et al., *Letters Appl. Microbiol.* 26:352-354 (1998)). The test also requires specific equipment for producing the ultraviolet rays. Further, this test may only be used to detect coliforms and *E. coli*. Other important microorganisms, such as the strain *E. coli* 0157 which is glucuronidase negative, are not detected, nor are other non-galactosidase-glucuronidase producing microorganisms.

The Violet Red Bile Agar (VRBA) method has been used to determine the quantity of both coliform and *E. coli* in a test sample. The test medium used in this method includes bile salts (to inhibit non-coliforms), lactose and the pH indicator neutral red. As coliforms (including *E. coli*) grow in the medium, the lactose is fermented with acid production, and the neutral red in the area of the bacterial colony becomes a brick red color. The results of this test are not always easy to interpret, and in order to determine the presence of *E. coli*, confirming follow-up tests, such as brilliant green lactose broth fermentation, growth in EC broth at 44.5° C. and streaking on Eosin Methylene Blue Agar (EMBA), must be performed.

The Membrane Filter (MF) method utilizes micropore filters through which samples are passed so that the bacteria are retained on the surface of the filter. This method is used most often when bacterial populations are very small, and a large sample is needed to get adequate numbers. The filter is then placed on the surface of a chosen medium, incubated, and the bacterial colonies growing on the membrane filter surface are counted and evaluated. This method is widely used and provides good results when combined with proper reagents and media. A disadvantage of this method is that it is expensive and time-consuming. It also does not work well with solid samples, or samples with high particulate counts.

The MF method can be used in conjunction with the inventive method described in this application.

The m-Endo method is also used to determine the quantity of *E. coli* and general coliforms and is an official USEPA approved method for testing water quality. The medium is commonly used with a membrane filter and *E. coli* and general coliform colony forming units (CFU) grow as dark colonies with a golden green metallic sheen. Due to a proven high rate of false positive error, typical colonies must be confirmed by additional testing. *Standard Methods for the Examination of water and Wastewater*, 20$^{th}$ Edition, 9-10 &9-60 (1998).

Other tests, such as the Most Probable Number (MPN), utilize lactose containing broths (LST, BGLB, EC) to estimate numbers of general coliforms and *E. coli*, but have also been shown to have high rates or error as well as being cumbersome and slow to produce results. Evans et al., *Appl. Envir. Microbiol.* 41:130-138 (1981).

The reagent 5-bromo-4-chloro-3-indolyl-β-galactopyranoside (X-gal) is a known test compound for identifying coliforms. When acted on by the β-galactosidase enzyme produced by coliforms, X-gal forms an insoluble indigo blue precipitate. X-gal can be incorporated into a nutrient medium such as an agar plate, and if a sample containing coliforms is present, the coliforms will grow as indigo blue colonies. X-gal has the advantage over the compound ONPG, described above, in that it forms a water insoluble precipitate rather than a diffusible compound, thereby enabling a quantitative determination of coliforms to be made when the test sample is incorporated into or onto a solidified medium, or when coliform colonies grow on the surface of a membrane filter resting on a pad saturated with a liquid medium or on a membrane filter resting on a solid medium. Further, it does not require the use of ultraviolet light.

A similar compound, 5-bromo-4-chloro-3-indolyl-β-D-glucuronide (X-gluc) is a known test compound for identifying *E. coli*. When acted on by the β-glucuronidase enzyme produced by most *E. coli*, X-gluc forms an insoluble indigo blue precipitate. X-gluc has the advantage over the compound MUG, described above, in that it forms a water insoluble precipitate, rather than a diffusible compound, thereby enabling a quantitative determination of *E. coli* to be made when the test sample is incorporated into or onto a solidified medium. X-gluc and its ability to identify *E. coli* are described in Watkins, et al., *Appl. Envir. Microbiol.* 54:1874-1875 (1988). A similar compound, indoxyl-β-D-glucuronide, which also produces sharp blue colonies of *E. coli*, was described in Leg, et al., *Can. J. Microbiol.* 34:690-693 (1987).

Although X-gal and X-gluc are each separately useful in the quantitative determination of either coliforms (X-gal) or *E. coli* (X-gluc), these indicator compounds have the disadvantage that they each contain the same chromogenic component. Therefore, they cannot be used together to identify and distinguish both *E. coli* and general coliforms in a single test with a single sample, since they both generate identically hued indigo blue colonies. A person using both reagents together would be able to quantitatively identify the total number of coliforms, the same as if X-gal were used alone, but would not be able to indicate which of the colonies were *E. coli* and which were other coliforms besides *E. coli*.

A recently developed and highly commercially successful test method and test medium for quantitatively identifying and differentiating general coliforms and *E. coli* in a test sample is described in U.S. Pat. Nos. 5,210,022, and 5,393, 662, both of which share common inventorship with the present application and which are hereby incorporated by reference. This method and test medium improves upon prior art methods by allowing the quantitative identification of general coliforms and *E. coli* in a single sample. Additional confirmatory tests are not necessary. The test sample is added to a medium containing a β-galactosidase substrate, such as 6-chloroindolyl-β-D-galactoside, and a β-glucuronidase substrate, such as 5-bromo-4-chloro-3-indolyl-β-D-glucuronide (X-gluc). The β-galactosidase substrate is capable of forming a water insoluble precipitate of a first color upon reacting with β-galactosidase, and the β-glucuronidase substrate is capable of forming a water insoluble precipitate of a second color, contrasting with the first color, upon reacting with β-glucuronidase. As a result, general coliforms may be quantified by enumerating the colonies of the first color (having β-galactosidase activity), and *E. coli* may be quantified by enumerating the colonies of the second color (having both β-galactosidase and β-glucuronidase activity). This technology has been widely copied.

Another recently developed test method and apparatus provides excellent results for the differentiation and identification of general coliforms, *E. coli* and *E. coli* 0157 strains and non-coliform Enterobacteriaceae. The method and test medium are described in U.S. Pat. No. 5,726,031, which shares common inventorship with the present application, and which is hereby incorporated by reference.

A certain class of substrates, referred to herein as "non-chromogenic," have been used to detect various microorganisms. A dipslide for detecting *E. coli* using hydroxyquinoline-β-D-glucuronide is disclosed by Dalet et al., *J. Clin. Microbiol*, 33(5):1395-8 (1995). Similarly, a technique for detection of *E. coli* in an agar-based medium using 8-hydroxyquinoline-β-D-glucuronide is disclosed by James et al., *Zentralbl Bakteriol Mikrobiol Hyg* [A], 267(3):316-21 (1988).

It is desirable to further improve the distinguishing colors generated in the test media. That is to say, in prior art test media which detect and distinguishing two biological entities, confusion may arise between the two colors which show in the media.

Further, it is desirable to be able to identify and differentiate other closely related organisms, such as members of the families Aeromonaceae, Vibrionaceae, and *Salmonella*. For example, the genus *Aeromonas* is closely related to coliforms and gives an almost identical biochemical test pattern. Further, the genus *Vibrio* is also an important type of bacteria that grows under the same general conditions as coliforms. It is known to distinguish *Aeromonas* colonies from general coliforms by testing all colonies in a given sample for the presence of cytochrome oxidase. Undesirably, however, this requires another set of tests. Further, *Aeromonas* is common in water and food, and it is commonly indicated in test samples as general coliforms, which results in high a false positive error for general coliforms by most current test methods. The *Aeromonas* can be prevented from interfering with the coliform results by adding certain antibiotics to the medium. However, the antibiotic amounts added must be carefully controlled. Further, the antibiotics which have been conventionally used have short life spans in the media so that they lose their potency quickly in other than a frozen condition. It may often be desirable to be able to culture, identify and enumerate *Aeromonas* spp. which cannot be done if they are inhibited.

Further, in those cases where it is desirable to inhibit *Aeromonas*, it is desirable for a better method of so doing, one in which the shelf life of the medium is not appreciably reduced by the inclusion of an inhibitor.

Additionally, it is also desirable to distinguish strains of *Salmonella* from *E. coli*, general coliforms and *Aeromonas*.

SUMMARY OF THE INVENTION

The present invention overcomes the disadvantages of prior art methods by providing a test method and medium for quantitatively or qualitatively identifying and differentiating biological entities in a test sample that may include a plurality of different biological entities.

In one embodiment, the present invention introduces the use of "nonchromogenic" substrates to enhance the distinction among multiple colors produced by distinct biological entities present in the inventive test medium. Unexpectedly, it has been discovered that other "chromogenic" substrates present in the inventive test medium do not interfere with the substantially black color achieved with the nonchromogenic substrate. That is to say, so long as a given biological entity is responsive to the nonchromogenic substrate, aggregations thereof present in the test medium will show as a substantially black color—independent of whether such biological entity is responsive to one, two or more chromogenic substrates which are also present in the medium. The present invention exploits this hitherto unexplored property of nonchromogenic substrates.

In one form thereof, the present invention provides a test medium for detecting, identifying and qualifying or quantifying first and second biological entities. The test medium includes a nutrient base medium including ions of a salt, a chromogenic substrate and a nonchromogenic substrate. The first biological entity is responsive to the nonchromogenic substrate whereas the second biological entity is responsive to the chromogenic substrate. In this test medium, aggregations of the first biological entity present in the test medium are substantially black and aggregations of the second biological entity present in the test medium are a second color, the second color being distinguishable from the substantially black.

In one form, the inventive test medium accounts for the first biological entity being responsive to the chromogenic substrate in addition to the nonchromogenic substrate. In such event, aggregations of the first biological entity present in the test medium will nonetheless show as substantially black.

Significantly, even though the aggregations of the first biological entity are responsive to both the first and second substrates in this form, these aggregations still show as substantially black in the test medium. That is, the chromogenic substrate does not interfere with the substantially black color. Advantageously, this property of nonchromogenic substrates allows several different biological entities to be identified and differentiated in a single medium, aggregations of each biological entity having a visually distinguishable color.

In another form of the above-described inventive medium, the medium further includes the antibiotic nalidixic acid to inhibit the growth of *Aeromonas*, spp. Advantageously, it has been found that nalidixic acid, as compared with cefsulodin, does not significantly reduce the shelf life of the test medium incorporating it.

In this connection, another form of the present invention provides a method of making a test medium for detecting at least one first type of biological entity and inhibiting a second type of biological entity from growing in the medium. The method includes the steps of combining desired substrates with a nutrient base medium; adding an inhibitor to the medium; and then sterilizing the medium by subjecting the medium to at least 100° C. Because the inhibitor is added as an initial step, subsequent sterile addition of inhibitor is unnecessary.

In another form thereof, the present invention provides a test medium for detecting, identifying and qualifying or quantifying first, second and third biological entities. The test medium includes a nutrient base medium including ions of a salt. First and second chromogenic substrates and a nonchromogenic substrate are provided in the test medium. The first and second biological entities are responsive to the first and the second chromogenic substrates, respectively, and the third biological entity is responsive to the nonchromogenic substrate. Aggregations of the first biological entity present in the test medium are a first color, aggregations of the second biological entity present in the test medium are a second color, and aggregations of the third biological entity present in the test medium are substantially black.

In one form, the inventive test medium accounts for the third biological entity being responsive to the first and/or the second chromogenic substrates in addition to the nonchromogenic substrate. In such event, aggregations of the third biological entity will nonetheless show as substantially black.

It should be appreciated that the use of a nonchromogenic substrate along with one or more chromogenic substrates synergistically increases the number of biological entities that can be detected and distinguished in a single medium and synergistically increases the possible color combinations for a given set of biological entities to be detected. Stated another way, including a nonchromogenic component as one of the substrates synergistically increases the degrees of freedom in selecting other substrates and corresponding colors for a test medium. This is so because an aggregation of the biological entity which is responsive to the nonchromogenic substrate will dependably show as substantially black. No combined color effects need be accounted for with the nonchromogenic substrates. For example, in a test medium including three chromogenic substrates and a nonchromogenic substrate, at least three combined color combination effects are avoided by using the one nonchromogenic component, as compared with using four chromogenic components.

The present invention, in another form thereof, provides a test medium capable of detecting, quantifying, and differentiating general coliforms and/or *E. coli* spp. under ambient light. The test medium comprises a nutrient based medium including a salt. A first substrate capable of forming a first water insoluble component of a first color in the presence of *E. coli* and the ions of the salt is provided in the medium. The first color is substantially black. A second substrate capable of forming a second water insoluble component of a second color in the presence of general coliforms is provided. The second color is visually distinguishable from the first color. Thus, colonies of *E. coli* present in the test medium are indicated by the first substantially black color and colonies of general coliforms are indicated by the second color.

In one form of the above invention, the test medium further includes a third substrate capable of forming a third water insoluble component of a third color in the presence of *Salmonella*. The third color is distinguishable from the first and second colors, whereby the test medium is capable of quantifying and/or differentiating *E. coli*, general coliforms and *Salmonella*. Further, the substrates are selected such that general coliforms present in the test medium will also react with the third substrate to form a water insoluble component which includes the third color. Consequently, general coliform colonies are indicated in the test medium as a fourth color, the fourth color being a combination of the second color and the third color. The fourth color is visually distinguishable from the first and third colors. Still further, the substrates can be selected such that *Aeromonas* spp. form an insoluble component of the second color by reacting with the second substrate, but not the first and third substrates. Thus, in the inventive test medium, *E. coli* colonies will be generally black, general coliform colonies will be the fourth color, *Aeromonas* colonies will be the second color and *Salmonella* colonies will be the third color.

In another form thereof, the present invention provides a method for detecting, quantifying and differentiating under ambient light general coliforms, *E. coli*, and at least one of the genera *Aeromonas* or *Salmonella* in a test sample. The method comprises the steps of providing a nutrient base medium including first, second and third substrates. Each of the substrates is capable of forming a water insoluble component in the presence of at least one of general coliforms, *E. coli, Aeromonas, Salmonella*. The substrates are selected such that colonies of *E. coli* produced in the test medium are a first color, colonies of general coliforms produced in the test medium are a second color, and colonies of one of *Aeromonas* and *Salmonella* produced in the test medium are a third color. Each of the colors are visually distinguishable. The test medium is inoculated with the test sample and then incubated. The test medium is then examined for the presence of first colonies having the first color, second colonies having the second color, and third colonies having the third color. The first colonies are *E. coli*, the second colonies are general coliforms, and the third colonies are one of *Aeromonas* or *Salmonella*.

In one form thereof, the inventive method further includes adding ions from a salt to the test medium to react with one or more of the substrates. In so doing, a precipitate is produced which shows as a substantially black color in the presence of the specific enzyme for that substrate. A preferred compound for forming the substantially black color in the presence of the ions of the salt consists of a β-D-glucuronide. These compounds release an aglycone when hydrolized which forms a substantially black insoluble complex in the presence of ions.

In another form of the inventive method, the method further comprises examining the test medium for the presence of fourth colonies having a fourth color, wherein the substrates are selected such that colonies of *Aeromonas* are the third color and colonies of *Salmonella* are the fourth color, the fourth color being visually distinguishable from the first, the second and the third colors. The substrates may be selected such that the first color is substantially black, the second color is substantially blue-violet, the third color is substantially red-pink and the fourth color is substantially teal-green.

In another form of the inventive method, the substrates are selected such that colonies of *Aeromonas* as well as colonies of *Plesiomonas* and *Vibrios* are indicated as the third color.

One embodiment of the present invention uses a nonchromogenic substrate along with one or more chromogenic substrates and thereby synergistically increases the degrees of design freedom in selecting colors for the inventive test medium. This is so because the chromogenic substrates do not interfere with the substantially black precipitate formed by the nonchromogenic substrate.

Another advantage of one embodiment of the present invention is that it enables the quantification, identification and differentiation of four (4) different bacterial strains simultaneously in a single test medium using a single test sample, under ambient lighting. Subsequent tests with their concomitant extra time spent and extra costs are avoided. Of course, the inventive test medium of the present invention could also be used purely for qualitative purposes, as a mere presence/absence (P/A) test.

In one embodiment, the substrates are selected such that the colors are easy to visually distinguish from one another without the need for UV light or other visual aids, other than, perhaps, magnification means. For example, in one embodiment, *E. coli* colonies are clearly indicated by a precipitate having a substantially black color, general coliform colonies are indicated by a blue-violet color, *Aeromonas* colonies are indicated by a red-pink color, and *Salmonella* colonies are indicated by a teal-green color. Because these colors are visually so distinct, confusion among the colors is greatly reduced as compared to prior art media. In one embodiment, MUGluc (4-methylumbelliferyl-Beta-D-glucuronic acid) is used in place of a nonchromogenic substrate. In this test medium, general coliforms would still be indicated by a blue-violet or grayish color. *Aeromonas* colonies indicated by a red-pink color and *Salmonella* colonies indicated by a teal-green color; however, *E. coli* colonies would look the same in visible light as general coliforms, but also would fluoresce a bright bluish color under a long wave UV light and this could be distinguished from the other colonies. Although, the fluorescent product would diffuse more quickly than chromogenic or nonchromogenic substrates and make quantifying the colonies of *E. coli* more difficult, the *E. coli* colonies can be detected at around 14 hours incubation time, and in any case will suffice as a presence/absence test for the *E. coli*.

In yet another embodiment of the invention, it has been found that three chromogenic substrates may be used if properly combined. For example, a β-glucuronide such as X-Gluc (5-bromo-4-chloro-3-indolyl-β-D-glucuronic acid) or Iodo-Gluc (5-iodo-3-indolyl-β-D-glucuronic acid) may be used with chromogenic α- and β-D-galactoside substrates. Examples of α- and β-galactoside substrates that may be suitable are 6-chloro-3-indolyl-β-D-galactoside and 5-bromo-4-chloro-3-indolyl-α-D-galactoside. In this embodiment, the β-D-glucuronide and α-D-galactoside substrates form the same general color in the presence of colonies that produce the respective enzymes; however, the colors may be distinguished by providing the substrates in different amounts so that the resulting color produced by one is darker than that produced by the other. In addition, even if the substrates are provided in approximately the same amounts, colonies that react to both the β-D-glucuronide and α-D-galactoside, such as *E. coli* should be darker that colonies such as general coliforms, which only react to the α-D-galactoside It should be appreciated, that it would not be necessary to add ions of salt if a nonchromogenic substrate is not used.

In an additional aspect of the present invention, MUGluc or another fluorescent glucuronide substrate may be combined in a test medium with a chromogenic or nonchromogenic glucuronide substrate. In this case, the MUGluc substrate can be used to detect *E. coli* under fluorescent light with less incubation time than is required to detect colonies with a chromogenic or nonchromogenic glucuronide. In addition, the MUGluc substrate can serve as a confirmation of the presence/absence of *E. coli*, if for any reasons there is some question as to the colors visible in ambient light produced by the colonies in the presence of the substrates.

Another advantage of the test medium of the present invention is its flexibility and ease of use. The incubation temperature is not critical as growth and differentiation of the organisms mentioned may occur within an optimum range. Therefore, resuscitation steps are avoided and inhibition of temperature sensitive strains does not occur. Also, inexpensive equipment may be used.

In one embodiment of the present invention, the color distinction obtained in a test medium can be intensified for identifying and differentiating *E. coli* from general coliforms. In one test medium, *E. coli* colonies present a substantially black color, whereas general coliforms present a red-pink color, the distinction therebetween being much more apparent than in prior art test media. Confusion between the two colors is therefore greatly reduced.

Still another advantage of the present invention is that it enables the identification and differentiation of *Aeromonas* spp. from general coliforms. Prior art test media undesirably require using a cefsulodin inhibitor for preventing *Aeromonas* spp. from growing therein. However, the use of cefsulodin as an inhibitor requires an extra step in the process, viz., sterile addition of filter sterilized antibiotic, and is difficult to control. Further, the presence of cefsulodin significantly reduces the effective shelf life of the medium. Further, the use of an inhibitor, obviously, prevents the detection and quantititification of *Aeromonas* spp. Advantageously, with the present invention, *Aeromonas* spp. can be detected, quantified and differentiated from general coliforms in a single medium.

As a related advantage, if it is nonetheless desired to inhibit colonies of *Aeromonas* spp. from growing in the test medium, the present invention provides a superior means for doing so. Specifically, preferred forms of the present invention employ nalidixic acid as an inhibitor, which has been shown to have a far less deleterious effect to the shelf-life of the medium incorporating it. Further, nalidixic acid can be added as part of the initial medium formulation prior to sterilization, thereby avoiding a costly and difficult process step which is required with cefsulodin. Finally, nalidixic acid is much less expensive than cefsulodin.

Another advantage of the present invention is that it can provide a test medium for qualitative or quantitative testing. That is, the test media in accordance with the present invention can be used as mere presence/absence test devices, or can be used to quantify various biological entities showing as different colored colonies on the inventive test media.

DETAILED DESCRIPTION OF THE INVENTION

The method and medium of the present invention allow the simultaneous detection, quantification, identification and differentiation of a variety of selected biological entities in a sample of mixed populations of biological entities. The inventive method and medium are particularly useful for the detection, quantification, identification and differentiation of *E. coli* and general coliforms, and further quantitative identification and differentiation of other selected biological entities, including *Aeromonas, Salmonella*, and *Vibrio* bacterial species.

The method and test media incorporating the present invention utilize the fact that the enzymatic activity of biological entities and specifically of bacteria varies with the genus, and/or family of bacteria of interest. The method and test media incorporating the present invention further utilize the fact that various enzyme identifying substrate complexes can be used to identify specific enzymes with the production of distinctive colors. Significantly, in one embodiment of the present invention, the method and test media incorporating the present invention exploit the fact that chromogenic substrates present in a test medium do not interfere with the substantially black color produced by nonchromogenic substrates.

While nonchromogenic substrates are known in the art, per se, their distinct properties vis-à-vis chromogenic substrates have been unrecognized. However, the behavior of a nonchromogenic substrate in a medium including the combination of chromogenic substrates is unique. To illustrate, aggregations of a biological entity which are responsive to two chromogenic substrates will typically show in a test medium as a combination of the two colors produced upon cleavage of the two respective substrates. When three chromogenic substrates are involved, as in another embodiment of the invention, the combined color effect is not obvious to predict and account for. Further, inherent variations in the amount of enzymes produced by particular strains of biological entities can result in different shades or hues of colors upon cleavage of the chromogenic substrates. Consequently, the colors can be difficult to distinguish for the lay person examining the test medium. Chromogenic substrates must therefore be chosen and used in a concentration in view of the other chromogenic substrates planned for inclusion in a given test medium.

Such is not the case with the nonchromogenic components. While aggregations of biological entities which are responsive to chromogenic substrates in addition to nonchromogenic substrates may show in the test medium as having a colored or fluoroescent "halo," such aggregations nonetheless appear substantially black and are therefore easy to identify. Multiple "degrees of freedom" are achieved with the nonchromogenic components.

Using a nonchromogenic substrate is one way of enabling a single test medium to differentiate four (4) different bacterial strains with four (4) visually distinguishable colors. The black color is difficult to mistake. Further, the substantially black pigmentation does not diffuse so that the location of the colonies is precisely known and the colonies can be accurately counted. The nonchromogenic substrates produce an insoluble chelated compound which is different than the dimer which is produced by the chromogenic substrates.

The inventive test medium and method allows not only a detection, quantification or qualitative identification and differentiation of general coliforms and *E. coli*, but also of *Salmonella* and *Aeromonas*, as well as *Plesiomonas* and *Vibrio*. *Plesiomonas* and *Vibrios* species are determined but not differentiated from *Aeromonas* species as they are very closely related.

DEFINITIONS

Biological entities, such as general coliforms, *E. coli.*, etc., are herein referred to as being "responsive" to certain chromogenic and nonchromogenic substrates. More specifically, a biological entity will predictably produce specific enzymes when the entity is present in a test medium such as the one described hereinbelow. These enzymes will selectively cleave chromogenic and nonchromogenic substrates. Upon cleavage, these substrates produce a color in the test medium. The mechanism for producing the color is different for chromogenic and nonchromogenic substrates, as described hereinbelow.

Microorganisms having β-galactosidase activity include those commonly known by the designation "coliform." There are various definitions of "coliform," but the generally accepted ones include bacteria which are members of the Enterobacteriaceae family, and have the ability to ferment the sugar lactose with the evolution of gas and acid. Most coliforms are positive for both α- and β-galactosidase. That is, they produce both α- and β-galactosidases.

Microorganisms having β-glucuronidase activity in addition to galactosidase activity primarily include most strains of *Escherichia coli*. That is, *E. coli* is positive for both α- and β-galactosidase as well as β-glucuronidase.

The term "general coliforms" as used in this application refers to coliforms other than the various strains of *E. coli*. These "general coliforms" are gram-negative, non-spore forming microorganisms generally having α- and β-galactosidase activity (i.e., lactose fermenters), but not having β-glucuronidase activity, and having the ability to ferment the sugar sorbitol.

For purposes of this specification, a "chromogenic substrate" is a substrate which needs no additional chemicals present in the test medium upon hydrolysis for color production. That is, a chromogenic substrate is cleaved by the specific enzyme corresponding to that substrate to form a dimer with the color being concentrated in the area of cleavage of the substrate. Many chromogenic substrates are known in the art. For purposes of this specification "chromogenic" includes fluorogenic substrates. The products of fluorogenic substrates require ultraviolet (UV) light to be detected and are more water soluble than other chromogenic substrates.

Certain substrates, referred to herein as "nonchromogenic," produce a dark, substantially black precipitate in the presence of ions of a salt and enzyme activity. For example, 8-hydroxyquinoline-β-D-glucuronide, when included in a medium along with a salt that produces ions, such as ferric ammonium citrate, will produce a substantially black precipitate in the presence of β-glucuronidase produced by *E. coli* or other biological entities. More specifically, upon cleavage of the nonchromogenic substrate by the particular enzyme, a substantially black water-insoluble complex forms in the medium. The substantially black precipitate consists of the ferric ions and the aglycone released when the substrate is hydrolized by the glucuronidase from *E. coli*. This precipitate is a chelated compound which does not diffuse. Nor is the substantially black color susceptible to interference from chromogenic compounds present in the test medium.

For purposes of this specification a "nonchromogenic substrate" means that a chemical in addition to those used with chromogenic components must be present in the test medium when the substrate is cleaved by its corresponding enzyme. The substantially black precipitate formed thereby is a combination of the substrate—salt complex and is not a dimer as is formed by the "chromogenic compounds."

For purposes of this specification, the expression "under ambient light" refers to the visible spectrum, i.e., colors which can be seen and distinguished with the naked eye. A colony present in a test medium which requires ultraviolet light to be seen, for example, would not fall under the definition "under ambient light". However, it is to be understood that the term "under ambient light" includes using a magnification device, if necessary. Magnification can be especially helpful when counting numerous colonies. The term "visually distinguishable" refers to two or more colors which can be differentiated under ambient light.

For purposes of this specification, the term "substantially black" includes dark brown to black, and also includes black with various colored halos, such as red-violet, green, fluorescent, etc.

For further purposes of this specification, color names recited herein are given as guidance, but it is to be understood that the color names are to be read broadly. That is, there can be overlap among the recited colors. This is because, as discussed, biological entities produce varying amounts of enzymes, which in turn affects the shade or hue of the resulting color.

The term "β-galactosidase substrate" as used herein refers to a β-galactoside comprising galactose joined by β-linkage to a substituent that forms a detectable compound when liberated by the action of β-galactosidase on the substrate. Similarly, the term "α-galactosidase substrate" as used herein refers to α-galactoside comprising galactose joined by α-linkage to a substituent that forms a detectable compound when liberated by the action of α-galactosidase on the substrate. The term "β-glucuronidase substrate" as used herein refers to a β-glucuronide comprising glucuronic acid joined by β-linkage to a substituent that forms a detectable precipitate when liberated by the action of β-glucuronidase on the substrate.

The α- and β-galactosidase substrates and compounds and any other substrates described herein as well as the β-glucuronidase substrates and compounds and any other substrates described herein may comprise carboxylate salts formed by reacting a suitable base with the appropriate galactoside or glucuronic carboxyl group. Suitable bases include alkali metal or alkaline earth metal hydroxides or carbonates, for example, sodium hydroxide, potassium hydroxide, calcium hydroxide, magnesium hydroxide, and corresponding carbonates; and nitrogen bases such as ammonia, and alkylamines such as trimethylamine, triethylamine and cyclohexylamine.

Designing a Test Medium for Specific Biological Entities

Certain members of the family Enterobacteriaceae can be distinguished by the presence of α-galactosidase activity in the absence of β-galactosidase activity, or vice-versa. For example, most *Salmonella* and *Shigella* spp. are positive for α-galactosidase, but negative for β-galactosidase. Similarly, *Aeromonas* spp. can be distinguished from other members of the family Enterobacteriaceae by the presence of β-galactosidase activity in the absence of α-galactosidase activity. The method and medium incorporating the present invention are designed to take advantage of these distinguishing characteristics. For example, the specificity of enzyme activity for *Salmonella* and *Aeromonas* spp., as opposed to general coliforms, can be exploited, as illustrated below.

The method described herein is particularly suitable for the detection, quantification or qualitative identification and differentiation of the different classes of microorganisms described previously, viz., general coliforms, *E. coli*, *Aeromonas* and *Salmonella*. Although the inventive method is particularly suitable for these particular microorganisms, it is not limited thereto. Instead, the techniques described herein have application to the identification and differentiation of a wide variety of biological entities.

That is, specific biological entities are "responsive" to various substrates. More particularly, these biological entities predictably produce or contain known enzymes. Substrates, either chromogenic or nonchromogenic, can be selected which, in the presence of a particular enzyme(s), will form a product of a predictable and distinguishable color. Multiple substrates can be selected to simultaneously identify a plurality of distinct biological entities in a single test medium, aggregations of each distinct entity being identifiable by a separate, distinguishable color. Further, while certain embodiments disclosed herein distinguish all of the various aggregations present in a test medium under ambient light, as that term is defined herein, such is not necessary. For example, several substrates disclosed herein require the use of ultraviolet light for the aggregations present in the medium to be seen.

Table I lists various enzymes whose presence may be detected using certain of the substrates listed in Table II.

TABLE I

Enzymes and Abbreviations

| | |
|---|---|
| Aara = α-D-arabinopyranosidase | Bglu = β-D-glucopyranosidase |
| Agal = α-D-galactopyranosidase | Bgluc = β-D-glucuronidase |
| Aglu = α-D-glucopyranosidase | Bman = β-D-mannopyranosidase |
| Bcel = β-D-cellopyranosidase | Bxyl = β-D-xylopyranosidase |
| Bfuc = β-D-fucopyranosidase | Nagal = N-acetyl-β- |
| Bgal = β-D-galactopyranosidase | D-galactopyranosidase |
| Afuc = α-D-fucopyranosidase | Naglu = N-acetyl-β- |
| Bxyl = β-D-xylopyranosidase | D-glucopyranosidase |
| Aman = α-D-mannopyranosidase | Bara = β-D-arabinopyranosidase |
| Axyl = α-D-xylopyranosidase | Acel = α-D-cellopyranosidase |
| esterase | Agluc = α-D-glucuronidase |
| | Nagluc = N-acetyl-β-D-glucuronidase |

TABLE II

Various Substrates and Color Upon Cleavage

| | |
|---|---|
| 6-chloro-3-indolyl substrates | Pink |
| 5-bromo-4-chloro-3-indolyl substrates | Teal |
| 3-indolyl substrates | Teal |
| N-methylindolyl substrates | Green |
| nitrophenyl substrates | Yellow |
| nitroaniline substrates | Yellow |
| 8-hydroxyquinoline substrates (and ion of salt) | Substantially black |
| cyclohexenoesculetin substrates (and ion of salt) | Substantially black |
| esculetin substrates (and ion of salt) | Substantially black |
| quinoline substrates (and ion of salt) | Substantially black |
| 5-Iodo-3-Indolyl substrates | Purple |
| 5-Bromo-6-Chloro-3-Indolyl substrates | Magenta |
| 6-Fluoro-3-Indolyl substrates | Pink |
| coumarin substrates | Fluorescent |
| fluorescein substrates | Fluorescent |
| rhodamine substrates | Fluorescent |
| resorufin substrates | Fluorescent |

Specific substrate compounds applicable for use with the test medium of the present invention are available as follows:

5-bromo-4-chloro-3-indolyl-β-D-galactopyranoside (X-gal) is a commercially available β-galactosidase substrate that produces an insoluble precipitate having an approximately teal color when reacted upon by β-galactosidase and is available from Biosynth International, Naperville, Ill.

6-chloro-3-indolyl-β-D-glucuronide is a compound which produces an insoluble precipitate having a magenta color, the preparation of which is described in the aforementioned incorporated by reference U.S. Pat. No. 5,210,022 and is available from Research Organics, Cleveland, Ohio.

The compound 5-bromo-4-chloro-3-indolyl-β-D-glucuronide (X-gluc) is a commercially available β-glucuronide that produces an insoluble precipitate having an approximately teal color when reacted upon by β-glucuronidase. Similarly, indoxyl-β-glucuronide is a similar compound, the preparation of which is described in the aforementioned article by Leg et al., in *Can J. Microbiol.*, the disclosure of which is incorporated by reference.

Another suitable β-galactoside is the compound 6-chloro-3-indolyl-β-D-galactoside which produces an insoluble precipitate having a pink/magenta color, the preparation of which is described in the aforementioned U.S. Pat. No. 5,210,022.

Other suitable compounds applicable as substrates in the practice of the present invention are specified in U.S. Pat. No. 5,210,022, all of which are incorporated herein by reference.

The substrate 8-hydroxyquinoline-β-D-glucuronide is a commercially available β-glucuronide that, in the presence of metallic ions such as iron, produces an insoluble precipitate having a substantially black color when reacted upon by β-glucuronidase and in the presence of other α- or β-galactoside substrates. 8-hydroxyquinoline-β-D-glucuronide is available from Biosynth International, Naperville, Ill.

Further, a salt providing ions suitable for use with the present invention is ferric ammonium citrate, available from Sigma Chemical, St. Louis, Mo. The cyclohexenoesculetin substrates are described in James et al., *Appl. & Envir. Micro.* 62:3868-3870 (1996) and in the presence of ferric ions, produce an insoluble substantially black precipitate.

N-methyl-indolyl substrates such as N-methylhydroxy-β-D-galactopyranoside are commercially available from Biosynth International, Naperville, Ill.

Nitrophenyl substrates, such as 2-nitrophenyl-β-D-galactopyranoside, are commercially available from Biosynth International, Naperville, Ill. Similarly, nitroaniline compounds are available for synthesis through Sigma Chemical, St. Louis, Mo.

Other substrates producing a substantially black color include esculetin substrates such as cyclohexenoesculetin-β-D-galactoside, which is described in James et al., *Appl. & Envir. Microbiol.* 62:3868-3870 (1996). Quinoline substrates, such as 8-hydroxyquinoline-β-D-galactopyranoside and 8-hydroxyquinoline-β-D-glucuronide are available through Biosynth International, Naperville, Ill.

Iodo-indolyl substrates, such as 5-iodo-3-indolyl-β-D-galactopyranoside are available through Biosynth International, Naperville, Ill.

Several fluorescent substrates are suitable for use with the present invention. Coumarin substrates such as 4-methylumbelliferyl substrates and 5-trifluoromethylumbelliferyl substrates are commercially available from Biosynth International, Naperville, Ill. Also suitable are fluorescein substrates, rhodamine substrates, and resorufin substrates. No commercial source is known for these three substrates but components are available from Sigma Chemical, St. Louis, Mo.

While specific examples of substrates suitable for use with the present invention have been enumerated hereinabove, such is not to be construed as limiting the invention in any manner. Instead, one of ordinary skill in the art can use Table IV and V hereinbelow to identify a virtually limitless number of substrates.

Preparation of Test Medium

The test medium is formed by combining the desired substrates with a nutrient base medium. The nutrient base medium can be any culture medium known in the art for providing the maintenance and reproduction of living cells. Generally, such media include nutrients, buffers, water, and sometimes a gelling agent. Possible gelling agents include agars, pectins, carrageenans, alginates, locust bean, and xanthins, among others.

The following is an example of the preparation of a test medium suitable for use in this invention. This example coincides with Example I, below.

The substrates 8-hydroxyquinoline-β-D-glucuronide, 5-Bromo-4-chloro-3-indolyl-α-D-galactopyranoside, and 6-Chloro-3-indolyl-β-D-galactopyranoside are added in quantities of 250 mg/L medium; 70 mg/L medium; and 175 mg/L medium, respectively. The substrates are added directly to the hot (75°-85° C.) medium (formula below) in a blender prior to sterilization.

Standard agar medium may be made by adding 15 gm of bacteriological quality agar gum to the following nutrient formula

| Pancreatic Digest of Casein | 5.0 gm |
|---|---|
| Yeast Extract | 3.0 gm |
| Dipotassium Phosphate | .3 gm |
| Deionized Water | 990 ml |
| Ferric Ammonium Citrate (sterilized separately from the other components) | 800 mg in 10 ml deionized water | and then sterilizing at 121° C. for 15 minutes. The medium should be adjusted to result in a pH of 7.0. The sterilized agar medium is allowed to drop to a temperature of 45° C. in a water bath and then the sterile solution containing the substrates prepared as described above is added. The medium is mixed thoroughly and poured into sterile petri plates at a volume of 20 ml/plate.

A pectin-based test medium may be prepared using the same steps described above except that 25 gm of low methoxyl pectin is used as the solidifying agent and the medium is poured at room temperature into petri plates containing a thin gel layer containing calcium ions which combine with the pectin to form a solid gel. A suitable pectin culture medium is described in U.S. Pat. No. 4,241,186 and U.S. Pat. No. 4,282,317, the disclosures of which are incorporated herein by reference. A pectin-based medium is preferred over a standard agar medium because it has the advantages of convenience and temperature independence for the user. The use of pectin media is well described and accepted as a result of AOAC collaborative studies and other published and in-house investigations.

A suitable pectin medium is commercially available from Micrology Laboratories, LLC under the trademark Easygel®. Aqueous based medium without gelling agent is available from Micrology Labs, Goshen Ind., for use with membrane filters.

Inoculation of the Test Medium with the Sample

The test medium may be inoculated with a sample to be tested for the presence of microorganisms by any method known in the art for inoculating a medium with a sample containing microorganisms. For example, the sample to be tested may be added to the petri plates prior to adding the nutrient base medium (pour plate technique) or spread on the surface of the plates after they have cooled and solidified (swab or streak plate technique). Liquid samples may also be filtered through a micropore (0.45 micrometer size) membrane filter which is then placed on the surface of a solid medium or on a pad saturated with the medium.

Incubation of the Test Medium

The inoculated test medium is incubated for a sufficient time and at such a temperature for individual microorganisms present in the sample to grow into detectable colonies. Suitable incubation conditions for growing microorganisms in a medium are known in the art. Commonly, the test medium is incubated for about 24-48 hours at a temperature of about 30°-40° C. Less incubation time may be required, such as about 14 hours, to obtain results for a fluorescent substrate.

Unless inhibitors of the general microbial population are used, the general microbial population as well as general coliforms, *E. coli, Aeromonas* spp., and *Salmonella* spp. and *Shigella* spp. will grow in the incubated test medium. Because the precipitates formed are insoluble (except for the fluorogenic substrates) in the test medium, they remain in the immediate vicinity of microorganisms producing the various enzymes. As the microorganisms reproduce to form colonies, the colonies show as colony forming units having the color produced by the particular substrate.

For example, *E. coli* produces β-galactosidase and α-galactosidase, but, unlike general coliforms and *Aeromonas* spp., also produces β-glucuronidase. Therefore, insoluble precipitates of each of the β-galactosidase substrate, the α-galactosidase substrate and the nonchromogenic β-glucuronide substrate are formed by the action of the respective enzymes such that colonies of *E. coli* show as a substantially black color, sometimes having a violet-blue halo therearound.

General coliforms produce β-galactosidase and α-galactosidase and consequently cleave both the α-galactosidase and β-galactosidase substrates. In the present example, the 5-Bromo-4-chloro-3-indolyl-α-D-galactoside substrate produces a blue-green or teal color, whereas the 6-Chloro-3-indolyl-β-D-galactoside produces a pink, or red-pink color. Thus, general coliform colonies will show as a blue-violet color, which is a combination of the colors produced by each of the α- and β-galactosides, respectively.

Significantly, however, it has been found that *Aeromonas* spp., which are closely related to coliforms, and give an almost identical biochemical test pattern, are β-galactosidase positive and α-galactosidase negative. That is, *Aeromonas* spp. will not hydrolize the α-galactoside substrate. Therefore, *Aeromonas* colonies present in the test medium will show as colonies having the pink-red color produced by the β-galactoside substrate.

Further, it has been found that members of the genus *Salmonella* are positive for α-galactosidase, but negative for β-galactosidase. That is, *Salmonella* will not hydrolize the β-galactosidase substrate. Therefore, colonies of *Salmonella* present in the test medium will appear as a teal, or blue-green color produced by the α-galactoside substrate.

Examination of the Test Medium and Enumeration of Microorganisms

The substrates selected for the above example produce three distinct colors, and general coliforms are indicated by a fourth color which is a combination of two of the three colors. That is, *E. coli* colonies show as substantially black, general coliform colonies show as blue-violet, *Aeromonas* colonies show as red-pink, and *Salmonella* colonies show as teal-green. While the individual shades of these colors may vary somewhat in the test medium due to factors such as varying enzyme production of the biological entities, it has been found that these four colors are distinct enough so that confusion amongst them is unlikely.

The colonies of each type of microorganism may be enumerated by counting the colonies or by other methods known in the art for enumerating microorganisms on a test plate. The number of colonies of each type generally indicates the number of microorganisms of each type originally present in the sample before incubation.

Optional Ingredients

Inhibitors

The method of the present invention does not require inhibitors. However, the medium may be made more selective for general coliforms and E. coli if desired by the addition of various compounds that are inhibitory to the general microbial population, but have little or no effect on coliforms. Following are some compounds which may be used: a) bile salts, about 0.3 g/liter, b) sodium lauryl sulfate, about 0.2 g/liter, c) sodium desoxycholate, about 0.2 g/liter, d) Tergitol 7, about 0.1 ml/liter. The use of one or more of these compounds reduces the background (non-coliform) microorganism presence and makes a less cluttered plate and eliminates the possibility of inhibition or interference by the non-coliform organisms in the sample. The use of certain antibiotics may accomplish the same result.

Cefsulodin is commonly used in currently available test media to inhibit Aeromonas spp. However, the use of cefsulodin as an inhibitor requires an extra step in the process, viz., sterile addition of filter sterilized antibiotic. This step is difficult to control. Further, the presence of cefsulodin significantly reduces the effective shelf life of the medium. It has been found that Nalidixic acid can be used instead of Cefsulodin to inhibit Aeromonas spp. with about the same efficacy. Nalidixic acid is preferable because it can survive the approximately 120° C. temperature reached in autoclaving the test media. Therefore, unlike cefsulodin, nalidixic acid can be added to the test media as part of the initial media formulation prior to sterilization (see, preparation of test medium, above). It also follows that the resistance of the nalidixic acid to unfavorable environmental conditions will result in a longer shelf life for a medium containing it as compared to cefsulodin.

Inducers

It is possible that the enzyme production of the general coliforms may be enhanced by the addition to the medium formulations of very small amounts of substances known as enzyme inducers. One specific inducer for β-galactosidase is available and is known chemically as isopropyl-β-thiogalactopyranoside. Adding approximately 100 mg/liter of medium has a positive and noticeable effect on the speed of enzyme production for some species of coliforms. Other enzyme inducers are available and may be added to media formulations if enhanced enzyme production is deemed helpful.

EXAMPLES

Listed below are broad examples of test media enzyme substrate combinations to be used in combination with the nutrient formula discussed above or other suitable nutrient formulas which may be prepared in practicing the present invention.

Table III illustrates the flexibility of the preferred embodiments incorporating the present invention. Table III is a matrix of some of the possible four-color combinations available for the preferred biological entities E. coli, general coliforms, and at least one of the genera Aeromonas or Salmonella to be detected by using the teachings of this disclosure. Other color combinations are possible. In many cases, a plurality of different substrates will achieve a desired result, the only difference being the colors detected for a specific enzyme. The preferred color choice for the detection of E. coli is denoted with an asterisk in Table III, depending on the colors chosen to detect other microorganisms. As discussed above, other chromogenic substrates do not interfere with the substantially black color, and the substantially black color is easy to distinguish from the other colors.

As discussed above, the use of Table III requires taking into account the combined color effect discussed above which is produced by the inclusion of multiple chromogenic substrates in a single medium. For example, with reference to the first entry in Table III, it can be understood that general coliforms will appear as a combination of (1) red-pink (magenta) and (2) teal, the resulting color being blue-violet. This is the case because general coliforms are responsive to two chromogenic substrates. Similarly, general coliforms will show in a test medium in accordance with the second entry of Table III as a combination of (1) red-pink (magenta) and (2) yellow.

TABLE III

Color possibilities for detection of preferred microorganisms desired color

| | red-pink or magenta | teal | green | yellow | black | fluorescent | fluorescent | fluorescent | dark blue/purple | light blue/gray |
|---|---|---|---|---|---|---|---|---|---|---|
| 1 | general coliforms Aeromonas | general coliforms Salmonella* | E. coli | E. coli | E. coli | E. coli | | | | |
| 2 | general coliforms Aeromonas | E. coli | E. coli | general coliforms Salmonella* | E. coli | E. coli | | | | |
| 3 | E. coli | general coliforms Aeromonas | E. coli | general coliforms Salmonella* | E. coli | E. coli | | | | |
| 4 | general coliforms Salmonella* | E. coli | general coliforms Aeromonas | E. coli | E. coli | E. coli | | | | |
| 5 | E. coli | general coliforms Salmonella* | general coliforms Aeromonas | E. coli | E. coli | E. coli | | | | |
| 6 | E. coli | E. coli | general coliforms Aeromonas | general coliforms Salmonella* | E. coli | E. coli | | | | |

TABLE III-continued

Color possibilities for detection of preferred microorganisms desired color

| | red-pink or magenta | teal | green | yellow | black | fluorescent | fluorescent | fluorescent | dark blue/purple | light blue/gray |
|---|---|---|---|---|---|---|---|---|---|---|
| 7 | E. coli | E. coli | E. coli | E. coli | general coliforms Aeromonas | general coliforms Salmonella* | E. coli | | | |
| 8 | general coliforms Aeromonas | E. coli | E. coli | E. coli | E. coli | general coliforms Salmonella* | E. coli | | | |
| 9 | E. coli | general coliforms Aeromonas | E. coli | E. coli | E. coli | general coliforms Salmonella* | E. coli | | | |
| 10 | E. coli | E. coli | general coliforms Aeromonas | E. coli | E. coli | general coliforms Salmonella* | E. coli | | | |
| 11 | E. coli | E. coli | E. coli | general coliforms Aeromonas | E. coli | general coliforms Salmonella* | E. coli | | | |
| 12 | general coliforms Aeromonas | E. coli | E. coli | E. coli | general coliforms Salmonella* | E. coli | | | | |
| 13 | E. coli | general coliforms Aeromonas | E. coli | E. coli | general coliforms Salmonella* | E. coli | | | | |
| 14 | E. coli | E. coli | general coliforms Aeromonas | E. coli | general coliforms Salmonella* | E. coli | | | | |
| 15 | E. coli | E. coli | E. coli | general coliforms Aeromonas | general coliforms Salmonella* | E. coli | | | | |
| 16 | E. coli | E. coli | E. coli | E. coli | E. coli | E. coli | general coliforms Aeromonas | general coliforms Salmonella* | | |
| 17 | Aeromonas | Salmonella | | | | E. coli | | | E. coli | general coliforms |

*Shigella may also show as this color.

Table IV is a partial list of enzyme patterns for biological entities preferred to be to be detected in accordance with the teachings of this disclosure. It is to be understood that one of ordinary skill in the art would readily recognized that other enzymes which are known and have been produced, and enzymes which are known only on a theoretically level, would also perform satisfactorily.

TABLE IV

| ENZYME NAME | E. coli | GENERAL COLIFORM | Aeromonas | Salmonella | Plesiomonas | Vibrio |
|---|---|---|---|---|---|---|
| Aara = α-D-arabinopyranosidase | + | + | − | + | | |
| Agal = α-D-galactopyranosidase | + | + | − | + | | |
| Aglu = α-D-glucopyranosidase | − | + | + | − | + | |
| Bcel = β-D-cellopyranosidase | − | + | − | − | − | − |
| Bfuc = β-D-fucopyranosidase | + | + | + | − | − | − |
| Bgal = β-D-galactopyranosidase | + | + | + | − | + | + |
| Bgal = β-D-glucopyranosidase | + | + | + | − | − | − |
| Bgluc = β-D-glucuronidase | + | − | − | − | − | − |
| Bman = β-D-mannopyranosidase | + | + | − | + | + | + |
| Bxyl = β-D-xylopyranosidase | − | + | − | − | | |
| Nagal = N-acetyl-β-D-galactopyranosidase | − | + | + | − | + | + |
| Naglu = N-acetyl-β-D-glucopyranosidase | − | + | + | − | + | + |

TABLE IV-continued

| ENZYME NAME | E. coli | GENERAL COLIFORM | Aeromonas | Salmonella | Plesiomonas | Vibrio |
|---|---|---|---|---|---|---|
| Aman = α-D-mannopyranosidase | − | − | − | − | − | − |
| esterase = esterase | − | − | − | + | − | − |

Table V is a matrix which teaches a wide variety of substrates and their associated colors for use in test media in accordance with the teachings of this disclosure. The left hand side of Table V indicates the color that will result when the listed chromogenic component is cleaved from its corresponding substrate by the specific enzyme for that substrate. In the case of the nonchromogenic components, the color is substantially black and the reaction mechanism requires the presence of ions of a salt upon cleavage of the substrate, as explained above.

Test enzymes which are produced by certain biological entities (see Table IV) are found at the right hand side of table V. "Substrate components" are shown to the left of the specific test enzymes. Each of the substrate components listed on the right hand side of table V can be combined with any of the chromogenic or nonchromogenic components listed on the left hand side of table V to identify a specific substrate for use in a test medium. It can therefore be understood that Table V teaches a large quantity of substrates possible for use in accordance with the present invention. Many of the substrates identified by the above-described use of table V are commercially available, whereas the method for producing other identified substrates is described in the literature. Still other substrates identified by using table V are only theoretically possible.

Nonchromogenic components are included at the bottom left hand side of Table V, and are different from the chromogenic components because they do not form specific colors upon cleavage. Instead, the quinoline or esculetin components combine with ions of a salt (e.g., ferric salt) which must be present in the medium when the substrate is cleaved by the specific enzyme. The substantially black precipitate formed by the nonchromogenic components is a combination of the quinoline or esculetin—iron complex rather than a dimer which is formed by the chromogenic components.

Unlike nonchromogenic components, the chromogenic components should be selected in view of all other chromogenic components selected for the medium and in view of the enzyme patterns of the entities to be detected. The selection and concentration of chromogenic components should maximize the distinction among the respective colors produced.

While many various chromogenic component and substrate component/enzyme possibilities are taught by Table V, other possibilities within the scope of the appended claims would be possible by one of ordinary skill in the art. For example, as shown in Table V, one of ordinary skill in the art could combine an N-acetyl group with many of the sugars of the substrate components listed in Table V. For example, an N-acetyl group could be combined with β-D-mannopyranoside to form N-acetyl-β-D-mannosaminide, the corresponding enzyme being N-acetyl-β-D-mannosaminidase. Any of the chromogenic components or nonchromogenic components listed on the left hand side of Table V could then be combined with the substrate component to identify a substrate. If the substrate is commercially available or the method of making it is known, the substrate could be used in a test medium. Upon cleavage of the substrate by the corresponding enzyme in the test medium, the color listed will appear.

Generally, the teachings of this disclosure can be used as follows to make a test medium for detecting various microorganisms or cell types. First, the microorganisms desired to be detected and differentiated are selected. The preferred organisms to be detected are E. coli, general coliforms, and at least one of the genera Aeromonas or Salmonella. Enzymes produced by the selected organisms can be identified with reference to Table IV. Equipped with knowledge of specific enzymes produced by each microorganism, one can then identify corresponding substrates components from the right hand side of Table V. Depending upon the color desired, one can select a chromogenic or nonchromogenic component from Table V to be combined with the substrate component to identify a substrate for inclusion in the test medium. If the substrate thereby identified is commercially available or the method of its synthesis is known, the substrate can be used in the test medium.

TABLE V

COLOR COMPONENT AND SUBSTRATE COMPONENT MATRIX

| CHROMOGENIC COMPONENT & | (COLOR) |
|---|---|
| 6-fluoro-3-indolyl- | (pink) |
| 6-chloro-3-indolyl- | (pink/red) |
| 5-bromo-6-chloro-3-indolyl- | (magenta) |
| 3-indolyl- | (teal) |
| 5-bromo-4-chloro-3-indolyl- | (teal) |
| 5-iodo-3-iondolyl- | (purple) |
| N-methylindolyl- | (green) |
| 4-methylumbelliferyl- | (fluorescent) |
| rhodamine- | (fluorescent) |
| fluorescein- | (fluorescent) |
| resorufin- | (fluorescent) |
| coumarin | (fluorescent) |
| nitrophenyl- | (yellow) |
| nitroaniline | (yellow) |

| NONCHROMOGENIC COMPONENT | (COLOR) |
|---|---|
| 8-hydroxyquinoline plus ions- | (substantially black) |
| 3,4-cyclohexenoesculetin plus ions | (substantially black) |
| esculetin plus ions- | (substantially black) |

| SUBSTRATE COMPONENT | TEST ENZYME |
|---|---|
| α-D-arabinopyranoside | Aara. |
| α-D-cellopyranoside | Acel. |
| α-D-fucopyranoside | Afuc. |
| α-D-galactopyranoside | Agal. |
| α-D-glucuronide | Agluc. |
| α-D-mannopyranoside | Aman. |
| α-D-xylopyranoside | Axyl. |

TABLE V-continued

COLOR COMPONENT AND SUBSTRATE COMPONENT MATRIX

| | |
|---|---|
| β-D-arabinopyranoside | Bara. |
| β-D-cellopyranoside | Bcel. |
| β-D-fucopyranoside | Bfuc. |
| β-D-galactopyranoside | Bgal. |
| β-D-glucopyranoside | Bglu. |
| β-D-glucuronide | Bgluc. |
| β-D-mannopyranoside | Bman. |
| β-D-xylopranoside | Bxyl. |
| N-acetyl-β-D-galactosaminide | Nagal |
| N-acetyl-β-D-glucosaminide | Naglu |
| N-acetyl-β-D-glucuronaminide | Nagluc |

TABLE V-continued

COLOR COMPONENT AND SUBSTRATE COMPONENT MATRIX

N-acetyl + other sugar components

| | |
|---|---|
| butyrate | esterase |
| caprylate | esterase |
| palmitate | esterase |

Table VI is a concise summary of the specific examples.

TABLE VI

EXAMPLE SUMMARIES

| Example # | Substrate | E. coli | General Coliforms | Aeromonas | Salmonella* |
|---|---|---|---|---|---|
| I | 8-hydroxyquinoline-β-D-glucuronide | X | | | |
| | 6-chloro-3-indolyl-β-D-galactopyranoside | X | X | X | |
| | 5-bromo-4-chloro-3-indolyl-α-D-galactopyranoside | X | X | | X |
| | color⇒ | Black | Purple-Blue | Pink | Teal |
| II | 8-hydroxyquinoline-β-D-glucuronide | X | | | |
| | 6-chloro-3-indolyl-β-D-galactopyranoside | X | X | X | |
| | 6-chloro-3-indolyl-β-D-mannoside | X | X | | X |
| | 5-bromo-4-chloro-3-indolyl-α-D-galactopyranoside | X | X | | X |
| | color⇒ | Black | Purple-blue | Red-pink | Purple-blue |
| IIIA | 8-hydroxyquinoline-β-D-glucuronide | X | | | |
| | 6-chloro-3-indolyl-β-D-galactopyranoside | X | X | X | |
| | 6-chloro-3-indolyl-α-D-galactopyranoside | X | X | | X |
| | 5-bromo-4-chloro-3-indolyl-β-D-galactopyranoside | X | X | X | |
| | color⇒ | Black | Purple-blue | Purple-blue | Pink |
| IIIB | 8-hydroxyquinoline-β-D-glucuronide | X | | | |
| | 6-chloro-3-indolyl-β-D-galactopyranoside | X | X | X | |
| | 5-bromo-4-chloro-3-indolyl-α-D-galactopyranoside | X | X | | X |
| | 5-bromo-4-chloro-3-indolyl-β-D-galactopyranoside | X | X | X | |
| | color⇒ | Black | Purple-blue | Purple-blue | Teal |
| IIIC | May eliminate Aeromonas with inhibitors which allows removal of 6-chloro-3-indolyl-β-D-galactopyranoside from Examples IIIA and IIIB | | | | |
| IV | 6-chloro-3-indolyl-β-D-galactopyranoside | X | X | X | |
| | 6-chloro-3-indolyl-β-D-mannoside | X | X | | X |
| | 5-bromo-4-chloro-3-indolyl-α-D-galactopyranoside | X | X | | X |
| | color⇒ | Purple-Blue | Purple-blue | Pink | Purple-blue |
| V-A | 6-chloro-3-indolyl-β-D-galactopyranoside | X | X | X | |
| | 6-chloro-3-indolyl-α-D-galactopyranoside | X | X | | X |
| | 5-bromo-4-chloro-3-indolyl-β-D-galactopyranoside | X | X | X | |
| | color⇒ | Purple-blue | Purple-blue | Purple-blue | Pink |
| V-B | 6-chloro-3-indolyl-β-D-galactopyranoside | X | X | X | |
| | 5-bromo-4-chloro-3-indolyl-α-D-galactopyranoside | X | X | | X |
| | 5-bromo-4-chloro-3-indolyl-β-D-galactopyranoside | X | X | X | |
| | color⇒ | Purple-blue | Purple-blue | Purple-blue | Teal |
| V-C | May eliminate Aeromonas with inhibitors which allows removal of substrate No. 1 from example V-A and allows removal of substrate No. 3 from example V-B | | | | |
| VI | 5-bromo-4-chloro-3-indolyl-α-D-galactopyranoside | X | X | | X |
| | 6-chloro-3-indolyl-β-D-galactopyranoside | X | X | X | |
| | color⇒ | Purple-blue | Purple-blue | Pink | Teal |
| VII | 8-hydroxyquinoline-β-D-glucuronide | X | | | |
| | 5-bromo-4-chloro-3-indolyl-α-D-galactopyranoside | X | X | | X |
| | 6-chloro-3-indolyl-N-acetyl-β-D-galactosaminide | | X | X | |
| | Note: In example 7, Vibrio and Plesiomonas also show as pink along with Aeromonas | | | | |
| | color⇒ | Black | Purple-blue | Pink (see note) | Teal |

TABLE VI-continued

EXAMPLE SUMMARIES

| Example # | Substrate | E. coli | General Coliforms | Aeromonas | Salmonella* |
|---|---|---|---|---|---|
| VIII | 8-hydroxyquinoline-β-D-glucuronide | X | | | |
| | 5-bromo-4-chloro-3-indolyl-α-D-galactopyranoside | X | X | | X |
| | 6-chloro-3-indolyl-β-D-mannoside | X | X | | X |
| | 6-chloro-3-indolyl-N-acetyl-β-D-galactosaminide | | X | X | |
| | Note: In example 8, *Vibrio* and *Plesiomonas* also show as pink along with *Aeromonas* | | | | |
| | color⇒ | Black | Purple-blue | Pink (see note) | Purple-blue |
| IX | 5-bromo-4-chloro-3-indolyl-α-D-galactopyranoside | X | X | | X |
| | 6-chloro-3-indolyl-β-D-galactopyranoside | X | X | X | |
| | 6-chloro-3-indolyl-N-acetyl-β-D-galactosaminide | | X | X | |
| | color⇒ | Purple-blue | Purple-blue | Pink | Teal |
| X | 6-chloro-3-indolyl-N-acetyl-β-D-galactosaminide | | X | X | |
| | 5-bromo-4-chloro-3-indolyl-α-D-galactopyranoside | X | X | | X |
| | 6-chloro-3-indolyl-β-D-galactopyranoside | X | X | X | |
| | Note: For example 10, *Vibrio* and *Plesiomonas* also show as pink along with *Aeromonas* | | | | |
| | color⇒ | Purple-blue | Purple-blue | Pink (see note) | Teal |
| XI | 8-hydroxyquinoline-β-D-glucuronide | X | | | |
| | 6-chloro-3-indolyl-β-D-galactopyranoside (or) | X | X | X | |
| | 5-bromo-6-chloro-3-indolyl-β-D-galactopyranoside | X | X | X | |
| | Note: In example 11, *Aeromonas* may be eliminated by adding inhibitors | | | | |
| | color⇒ | Black | Pink Teal or | Pink Teal or | Not detected |
| XII | 8-hydroxyquinoline-β-D-galactopyranoside | X | X | X | |
| | 5-bromo-4-chloro-3-indolyl-α-D-galactopyranoside (or) | X | X | | X |
| | 6-chloro-3-indolyl-α-D-galactopyranoside | X | X | | X |
| | Note: In example 13, *Aeromonas* may be eliminated by adding an inhibitor | | | | |
| | color⇒ | Black | Black | Black | Teal or Pink |
| XIII | Use same substrates as in example No. 1, and add: 4-methyl-umbelliferyl-β-D-xylopyranoside | *Enterobacter* and *Klebsiella* showing as black colonies will fluoresce, thereby allowing reduction in false positive count of *E. coli*. | | | |
| XIV | 8-hydroxy-quinoline-β-D-glucuronide | X | | | |
| | 6-chloro-3-indolyl-caprylate | | | | X |
| | color⇒ | Black | | | Red-pink |
| XV | 8-hydroxy-quinoline-β-D-glucuronide | X | | | |
| | 5-bromo-4-chloro-3-indolyl-caprylate | | | | X |
| | 6-chloro-3-indolyl-α-D-galactopyranoside | X | X | | X |
| | color⇒ | Black | Red-pink | | Blue-violet |
| XVI | 8-hydroxy-quinoline-β-D-glucuronide | X | | | |
| | 5-bromo-4-chloro-3-indolyl-β-D-galactopyranoside (or) | X | X | Inhibitor present | |
| | 5-bromo-6-chloro-3-indolyl-β-D-galactopyranoside | X | X | | |
| | color⇒ | Black | Teal (or) Magenta | | |
| XVII | 5-bromo-4-chloro-3-indolyl-β-D-glucuronide | X | | | |
| | 6-chloro-3-indolyl-β-D-galactopyranoside | X | X | X | |
| | 5-bromo-4-chloro-3-indolyl-α-D-galactopyranoside | X | X | | x |
| | color⇒ | Dark Purple/Blue | Light Blue-Gray | Pink | Teal |
| XVIII | 5-iodo-3-indolyl-β-D-glucuronide | X | | | |
| | 6-chloro-3-indolyl-β-D-galactopyranoside | X | X | X | |
| | 5-bromo-4-chloro-3-indolyl-α-D-galactopyranoside | X | X | | X |
| | color⇒ | Dark Purple | Light Blue-Gray | Pink | Teal |

TABLE VI-continued

EXAMPLE SUMMARIES

| Example # | Substrate | E. coli | General Coliforms | Aeromonas | Salmonella* |
|---|---|---|---|---|---|
| XIX | indoxyl-β-D-glucuronide | X | | | |
| | 6-chloro-3-indolyl-β-D-galactopyranoside | X | X | X | |
| | 5-bromo-4-chloro-3-indolyl-α-D-galactopyranoside | X | X | | X |
| | color⇒ | Dark Blue/ Purple | Light Blue-Gray | Pink | Teal |
| XX | 4-methylumbelliferyl-β-D-glucuronide | X | | | |
| | 6-chloro-3-indolyl-β-D-galactopyranoside | X | X | X | |
| | 5-bromo-4-chloro-3-indolyl-α-D-galactopyranoside | X | X | | X |
| | color⇒ | Fluoresce under UV | Light Blue-Gray | Pink | Teal |
| XXI | Use same substrates as in example No. XVII–XIX, and add: 4-methyl-umbelliferyl-β-D-glucuronide | X | X | X | X |
| | color⇒ | Dark Blue/ Purple and fluoresce | Light Blue-Gray | Pink | Teal |

*Shigella may also be indicated as this color

Example I

The microorganisms chosen to be identified, quantified and differentiated are E. coli, general coliforms, Aeromonas and/or Salmonella.

With reference to Table IV, E. coli produces the enzyme Bgluc, and Bgluc is not produced by any of the other microorganisms desired to be detected. With reference to the right hand side of Table V, it can be seen that the test enzyme Bgluc has a corresponding substrate component of β-D-glucuronide. Thus, a chromogenic or nonchromogenic component which produces a distinct color upon cleavage of Bgluc should be chosen from the left hand side of Table V. 8-hydroxyquinoline is chosen for its preferred substantially black color. The first identified substrate is therefore 8-hydroxyquinoline-β-D-glucuronide, the availability of which is described above. A metallic salt such as ferric ammonium citrate is also required and is added to the test medium so that, upon cleavage of the substrate by Bgluc, a substantially black water-insoluble complex forms in the medium. The substantially black precipitate consists of the ferric ions and the aglycone released when the substrate is hydrolyzed by the glucuronidase from E. coli.

With further reference to Table IV, Bgal, Bfuc and Bglu are common to Aeromonas and general coliforms. However, as indicated in Table IV, Bgal, Bfuc and Bglu are not produced generally by Salmonella. Therefore, a substrate component corresponding to one of Bgal, Bfuc and Bglu can be selected form the right hand side of Table V. Bgal and the associated substrate component β-D-galactopyranoside are chosen. The 6-chloro-3-indolyl-chromogenic component produces a red-pink color upon cleavage from its substrate in the presence of Bgal and is selected as the chromogenic component. The second substrate is therefore 6-chloro-3-indolyl-β-D-galactopyranoside.

Again referring to Table IV, Bman, Aara and Agal are common to Salmonella and general coliforms. However, as indicated in Table IV, Bman, Aara and Agal are not produced by Aeromonas. Thus, one of Bman, Aara and Agal can be chosen and its associated substrate component identified with reference to Table V. The test enzyme Agal and the respective substrate component α-D-galactopyranoside are chosen. Next, a chromogenic component must be selected from Table V. As shown on the left hand side of Table V, the chromogenic component 5-bromo-4-chloro-3-indolyl produces a teal color upon cleavage from its associated substrate and is therefore selected. The third substrate is therefore 5-bromo-4-chloro-3-indolyl-α-D-galactopyranoside.

General coliforms have a wide enzyme pattern which is responsive to both the 6-chloro-3-indolyl-β-D-galactopyranoside substrate and the 5-bromo-4-chloro-3-indolyl-α-D-galactopyranoside substrate. Therefore, general coliforms will show as a fourth distinct color which is a combination of the colors produced by the two aforementioned substrates, respectively. In this case the fourth color will be violet-blue, which is a combination of red-pink and teal.

Finally, as seen in Table IV, E. coli also exhibits a wide enzyme pattern and responsive to all three of the substrates chosen in this example, viz., 8-hydroxyquinoline-β-D-glucuronide, 6-chloro-3-indolyl-β-D-galactopyranoside, and 5-bromo-4-chloro-3-indolyl-α-D-galactopyranoside. Nonetheless, E. coli colonies present in the test medium will show as a substantially black color because, as discussed above, the chromogenic substrates do not interfere with the substantially black color. Advantageously, this substantially black color provides a superior means for distinguishing the E. coli, as well as allows four separate microorganisms to be detected, quantified, differentiated and identified in a single test medium. See Table VI.

Example II

The selected microorganisms to be detected, quantified, differentiated and identified are E. coli as a first color; general coliforms and Salmonella as a second color; and Aeromonas as a third color.

With reference to Table IV, E. coli produces the enzyme Bgluc, and Bgluc is not produced by any of the other microorganisms desired to be detected. With reference to the right hand side of Table V, it can be seen that the test enzyme Bgluc has a corresponding substrate component of β-D-glucuronide. Thus, a chromogenic or nonchromogenic component which produces a distinct color upon cleavage of Bgluc should be chosen from the left hand side of Table V. 8-hydroxyquinoline is chosen for its preferred substantially black color. The first identified substrate is therefore 8-hydroxyquinoline-β-D-glucuronide, the availability of which is described above. A metallic salt such as ferric ammonium citrate is also required and is added to the test medium so that, upon cleavage of the substrate by Bgluc, a substantially black water-insoluble complex forms in the medium. The substantially black precipitate consists of the ferric ions and the aglycone released when the substrate is hydrolized by the glucuronidase from *E. coli*.

With further reference to Table IV, Bgal, Bfuc and Bglu are common to *Aeromonas* and general coliforms. However, as indicated in Table IV, Bgal, Bfuc and Bglu are not produced by *Salmonella*. Using Table V in the fashion described above, 6-Chloro-3-indolyl-β-D-galactopyranoside is selected as the second substrate, which will produce a red-pink color upon cleavage as indicated by the chromogenic component list of Table V.

As seen in Table IV, the enzyme Bman is common to *Salmonella* but not *Aeromonas*. From table V, the substrate component associated with Bman is β-D-mannopyranoside. In this example, it is desired to also produce the second distinct color (red-pink) with *Salmonella* so that, ultimately, *Salmonella* colonies present in the test medium will show as the same color as general coliforms present in the test medium. Thus, the chromogenic component is 6-Chloro-3-indolyl- and the third substrate is therefore 6-Chloro-3-indolyl-β-D-mannopyranoside.

In this example, again using Table V, a fourth substrate is identified that will be cleaved by one of the enzymes Bman, Aara, Agal common to *Salmonella* to produce a third distinct color. Using table V in the fashion described above, the fourth substrate selected is 5-Bromo-4-chloro-3-indolyl-α-D-galactopyranoside, which produces a teal-green color in the presence of Agal common to *Salmonella*.

The resulting colors of colonies present in the test medium can be predicted as follows. *E. coli* exhibits a wide enzyme pattern that is positive for all four of the substrates chosen in this example, including the 8-hydroxy-glucuronide substrate which produces a substantially black color upon cleavage in the presence of the ions of the ferric salt. *E. coli* colonies show as substantially black. *Aeromonas* has an enzyme pattern which reacts with only the 6-Chloro-3-indolyl-β-D-galactopyranoside substrate chosen in this example and therefore colonies of *Aeromonas* show as red-pink. *Salmonella* has an enzyme pattern which cleaves both the third and fourth substrates selected in this example and therefore colonies of *Salmonella* show as purple-blue (a combination of teal and red-pink). Finally, general coliforms are positive for each of the second, third and fourth substrates selected and colonies thereof show as purple-blue, indistinguishable from the *Salmonella* colonies. As discussed above, different strains of all species of the various genera will not all produce the same amounts of the various enzymes, so there may be slight variations in shades of purple-blue, for example.

Example IIIA

The selected microorganisms to be quantified and differentiated in this example are *E. coli* as a first color, general coliforms and *Aeromonas* as a second color, and *Salmonella* as a third color.

With reference to Table IV, *E. coli* produces the enzyme Bgluc, and Bgluc is not produced by any of the other microorganisms desired to be detected. With reference to the right hand side of Table V, it can be seen that the test enzyme Bgluc has a corresponding substrate component of β-D-glucuronide. Thus, a chromogenic or nonchromogenic component which produces a distinct color upon cleavage of Bgluc should be chosen from the left hand side of Table V. 8-hydroxyquinoline is chosen for its preferred substantially black color. The first identified substrate is therefore 8-hydroxyquinoline-β-D-glucuronide, the availability of which is described above. A metallic salt such as ferric ammonium citrate is also required and is added to the test medium so that, upon cleavage of the substrate by Bgluc, a substantially black water-insoluble complex forms in the medium. The substantially black precipitate consists of the ferric ions and the aglycone released when the substrate is hydrolized by the glucuronidase from *E. coli*.

Using tables IV and V in a fashion similar to that described above with reference to Examples I and II, 6-Chloro-3-indolyl-β-D-galactopyranoside is selected as a second substrate to combine with one of the enzymes Bgal, Bfuc and Bglu common to coliforms and *Aeromonas*, but negative for *Salmonella* to produce a second distinct color, in this case substantially red-pink.

Similarly, 6-Chloro-3-indolyl-α-D-galactopyranoside is selected as a third substrate to combine with Agal, which is common to coliforms and *Salmonella*, but negative for *Aeromonas*. Upon reaction with the enzyme, this substrate will also produce the same distinct second color, namely red-pink.

5-Bromo-4-chloro-3-indolyl-β-D-galactopyranoside is selected as a fourth substrate to combine with the enzyme Bgal, which is common to coliforms and *Aeromonas*, but negative for *Salmonella*. This fourth substrate produces a teal-green color upon reaction with Bgal.

The resulting colors of colonies present in the test medium can be predicted as follows. *E. coli* exhibits a wide enzyme pattern and is positive for all four of the substrates chosen in this example. Therefore, *E. coli* colonies will show as substantially black. General coliform colonies have an enzyme pattern which is positive for the second, third and fourth substrates, so that general coliforms colonies show as purple-blue. *Aeromonas* colonies have an enzyme pattern which is positive for the second and fourth substrates chosen so that *Aeromonas* colonies also show as purple-blue. Finally, the enzymes common to *Salmonella* are only positive for the third of the four substrates, so that *Salmonella* colonies show as red-pink.

Example IIIB

As a variation, the test medium of Example IIIA can be prepared such that colonies of *Salmonella* will show as teal instead of pink-red, all of the other colony colors being the same as Example IIIA. With reference to Table VI, such can be accomplished by replacing the 6-chloro-3-indolyl-α-D-galactopyranoside of Example IIIA with 5-bromo-4-chloro-3-indolyl-α-D-galactopyranoside.

Example IIIC

A second, independent method for producing the same three colors as Example IIIA for the same four components can be achieved by adding nalidixic acid or other antibiotics or inhibitors of *Aeromonas* to the components listed in Example 1. In so doing, the cefsulodin or nalidixic acid or other substance acts as an inhibitor for *Aeromonas* so *Aeromonas* colonies do not grow. If *Aeromonas* is eliminated, then the purple-blue colonies are all true coliforms. If not eliminated, any *Aeromonas* will be counted as part of the coliforms which some persons may prefer since *Aeromonas* is an important indicator organism.

Example IV

In this example, the selected microorganisms to be detected, quantified and differentiated are *E. coli*, coliforms and *Salmonella* as a first distinct color and *Aeromonas* as a second distinct color. One test medium which achieves this result is the test medium described in Example II, except that the first substrate and metallic salt are omitted. Thus, because the enzyme pattern of *E. coli* reacts with the same substrates as the enzyme pattern for general coliforms, *E. coli* and general coliforms will be the same color in this test medium. Specifically, *E. coli*, coliforms and *Salmonella* colonies will show as a purple-blue color, whereas *Aeromonas* colonies will show as a substantially red-pink color.

Example V

The selected microorganisms to be detected, quantified and differentiated are *E. coli*, general coliforms and *Aeromonas* as a first distinct color, and *Salmonella* as a second distinct color. One test medium which achieves this result is the test medium of Example 3 with the first substrate and metallic salt being omitted. In this test medium, *E. coli*, general coliforms and *Aeromonas* colonies will show as a generally purple-blue color, whereas *Salmonella* colonies will show as a generally teal-green color or as a red-pink color.

Optionally, the 6-chloro-3-indolyl-α-D-galactoside can be replaced with 5-bromo-4-chloro-3-indolyl-β-D-galactoside so that *Salmonella* colonies show as teal, rather than pink.

A third way to achieve the same result is with an antibiotic, preferably nalidixic acid, to inhibit the growth of *Aeromonas* colonies. If *Aeromonas* is eliminated, then the purple-blue colonies are all true coliforms. If not eliminated, any *Aeromonas* will be counted as part of the coliforms which some persons may prefer since *Aeromonas* is an important indicator organism.

Example VI

The selected microorganisms to be detected, quantified and differentiated are *E. coli* and coliforms as a first distinct color, *Aeromonas* as a second distinct color and *Salmonella* as a third distinct color. A test medium which achieves this result is the test medium of Example I with the first substrate and metallic salt being omitted. In such a test medium, *E. coli* and general coliform colonies will show as purple-blue, *Aeromonas* colonies will show as generally red-pink, and *Salmonella* colonies will show as generally teal-green.

Example VII

The selected microorganisms to be detected, quantified and differentiated are *E. coli* as a first distinct color which is substantially black; general coliforms as a second distinct color which is substantially purple-blue; *Aeromonas/Vibrio/Plesiomonas* as a third distinct color which is substantially red-pink; and *Salmonella* as a fourth distinct color which is substantially teal-green.

With reference to Table IV, *E. coli* produces the enzyme Bgluc, and Bgluc is not produced by any of the other microorganisms desired to be detected. Therefore, a substrate which produces a distinct color upon cleavage of Bgluc should be chosen from Table V. 8-hydroxyquinoline-β-D-glucuronide produces a substantially black color in the presence of Bgluc and would be the preferred choice of substrate, as explained below. A metallic salt such as ferric ammonium citrate is also added to form a substantially black water insoluble complex consisting of the ferric ions and the aglycone released when the substrate is hydrolyzed by the glucuronidase from *E. coli*.

With further reference to Table IV, it can be seen that the enzyme Ngal and Naglu are common to the microorganisms *Aeromonas*, *Plesiomonas*, and *Vibrios*. Therefore, a suitable substrate for testing all of these microorganisms as a single distinct color is 6-chloro-3-indolyl-N-acetyl-β-D-galactosaminide, which produces a substantially red-pink color in the presence of these enzymes.

Again referring to Table IV, Bman, Aara and Agal are common to *Salmonella* and general coliforms. However, as indicated in Table IV, Bman, Aara and Agal are not produced by *Aeromonas*. Therefore, a substrate can be selected from Table V which reacts with one of Bman, Aara and Agal to produce a third distinct color. As shown in Table V, 5-bromo-4-chloro-3-indolyl-α-D-galactoside produces a teal-green color in the presence of Agal and is therefore selected as a substrate.

In this test medium *E. coli* colonies will show as substantially black, general coliform colonies will show as substantially purple-blue, *Aeromonas*, *Vibrio* and *Plesiomonas* colonies will show as substantially red-pink, and *Salmonella* colonies will show as substantially teal.

Example VIII

The selected microorganisms to be detected, quantified and differentiated are *E. coli* as a first distinct color; coliforms and *Salmonella* as a second distinct color; and *Aeromonas*, *Vibrio* and *Plesiomonas* as a third distinct color. One test medium for achieving this result is the test medium of Example 2, except that the fourth substrate chosen is 6-Chloro-3-indolyl-N-acetyl-α-D-galactosaminide, to which each of the microorganisms *Plesiomonas*, *Vibrios* and *Aeromonas* are responsive so that each of these colonies shows as a generally red-pink color.

Example IX

The selected microorganisms to be detected, quantified and differentiated in this example are *E. coli* and general coliforms as a first distinct color which is purple-blue; *Aeromonas*, *Plesiomonas*, and *Vibrios* as a second distinct color which is red-pink; and *Salmonella* as a third distinct color which is teal-green. This result can be achieved with the test medium as described in Example 6 with the addition of 6-Chloro-3-indolyl-N-acetyl-β-D-galactosaminide, to which each of the microorganisms *Plesiomonas*, *Vibrio* and *Aeromonas* is responsive.

Example X

The selected microorganisms to be detected, quantified and differentiated in this example are *E. coli* and general coliforms as a first color; *Aeromonas*, *Vibrio* and *Plesiomonas* as a second distinct color; and *Salmonella* as a third distinct color. A suitable test medium that achieves this result is the test medium disclosed in Example 7 except that the first substrate for detecting *E. coli* colonies is omitted. In this example, *E. coli* and general coliform colonies show as generally purple-blue, *Aeromonas, Vibrio* and *Plesiomonas* show as generally red-pink, and *Salmonella* show as generally teal-green. The addition of 6-Chloro-3-indolyl-β-D-galactopyranoside is necessary to yield the purple-blue color for *E. coli* colonies.

Example XI

The selected microorganisms to be detected, quantified and differentiated in this example are *E. coli* as a substantially black color and general coliforms as a red-pink color. With reference to Table IV, *E. coli* produces the enzyme Bgluc, and Bgluc is not produced by any of the other microorganisms desired to be detected. Therefore, a substrate which produces a distinct color upon cleavage of Bgluc should be chosen from Table V. 8-hydroxyquinoline-β-D-glucuronide produces a dark color in the presence of Bgluc and would be the preferred choice of substrate. A metallic salt such as ferric ammonium citrate is also added to form a black water insoluble complex consisting of ferric ions and the aglycone released when the substrate is hydrolized by glucuronidase from *E. coli*.

With further reference to Table IV, Bgal, Bfuc and Bglu are common to *Aeromonas* and general coliforms. However, as indicated in Table IV, Bgal, Bfuc and Bglu are not generally produced by *Salmonella*. Therefore, a substrate can be selected from Table V which reacts with one of Bgal, Bfuc and Bglu to produce a second distinct color. 6-chloro-3-indolyl-β-D-galactopyranoside produces a pink color in the presence of Bgal and is selected as the second substrate.

Optionally, the 6-chloro-3-indolyl-β-D-galactopyranoside can be replaced with 5-bromo-6-chloro-3-indolyl-β-D-galactopyranoside so that *Aeromonas* and general coliform colonies show as teal instead of pink.

As noted, the second substrate selected will result in colonies of *Aeromonas* also showing as a generally red-pink color. To avoid growth of *Aeromonas* colonies, an inhibitor, preferably nalidixic acid, is added. Thus, colonies of *E. coli* will show as substantially black, whereas colonies of general coliforms will show as a red-pink color.

Example XII

The selected microorganisms to be detected, quantified and differentiated in this example are *E. coli*, general coliforms and *Aeromonas* spp. as a substantially black color and *Salmonella* spp. as a second distinct color. The first substrate selected is 8-hydroxyquinoline-β-D-galactoside, which results in colonies of *E. coli*, general coliforms and *Aeromonas* showing as substantially black. The second substrate chosen can be either 5-Bromo-4-chloro-3-indolyl-α-D-galactopyranoside or 6-chloro-3-indolyl-α-D-galactopyranoside. If the former of these two substrates is chosen, colonies of *Salmonella* will show as a teal color, whereas if the latter of the two aforementioned substrates is chosen, colonies of *Salmonella* will show as a red-pink color.

Optionally, in this example, *Aeromonas* may be eliminated by adding an inhibitor, preferably nalidixic acid, as discussed in detail above.

Example XIII

The selected microorganisms to be detected, quantified and differentiated in this example are the same as in Example 1, except that this example illustrates a correction for false positives. That is, it is possible that certain unusual *Enterobacter* and *Klebsiella* spp. will show as black colonies along with *E. coli* in the test medium disclosed in Example 1. Thus, the count of *E. coli* could be inaccurately high.

In this example, 4-methyl-umbrelliferyl-β-D-xylopyranoside is added to the test medium described in Example 1. In so doing, *Enterobacter* and *Klebsiella* spp. showing as black colonies will also fluoresce, thereby allowing reduction in the false positive count of *E. coli*. This example illustrates the flexibility of embodiments incorporating the present invention. The fluoroescent component does not interfere with the substantially black color so that the black colonies are easily distinguished with the naked eye. Yet, under ultraviolet light, false positives can be detected and substantially reduced by examining the black colonies for fluorescence.

Example XIV

The selected microorganisms to be detected, quantified, differentiated and identified are *E. coli* as a substantially black color and *Salmonella* spp. as pink-red. General coliforms are colorless in this example.

With reference to Example I, E.coli is responsive to 8-hydroxy-quinoline-β-D-glucuronide. General coliforms, *Salmonella* and *Aeromonas* are not responsive to 8-hydroxy-quinoline-β-D-glucuronide. Thus, the first substrate chosen is 8-hydroxy-quinoline-β-D-glucuronide.

With reference to table IV, esterase enzyme is positive for *Salmonella* spp., but not any of the other preferred microorganisms to be detected. With reference to table V, the substrate 6-chloro-3-indolyl-caprylate can be identified, and will produce a pink-red color upon cleavage, and is therefore chosen as the second substrate.

In this test medium, colonies of *E. coli* will show as substantially black and colonies of *Salmonella* will show as pink-red.

Example XV

The selected microorganisms to be detected, quantified, differentiated and identified are *E. coli* as a substantially black color, *Salmonella*spp. as dark blue-purple, and general coliforms as red-pink.

With reference to Example I, *E. coli* is responsive to 8-hydroxy-quinoline-β-D-glucuronide. General coliforms, *Salmonella* and *Aeromonas* are not responsive to 8-hydroxy-quinoline-β-D-glucuronide. Thus, the first substrate chosen is 8-hydroxy-quinoline-β-D-glucuronide.

With reference to tables IV and V, 5-bromo-4-chloro-3-indolyl-caprylate can be identified as the second substrate to which *Salmonella* will be responsive. With further reference to Table V, 5-bromo-4-chloro-3-indolyl-caprylate forms a teal color upon cleavage.

6-chloro-3-indolyl-α-D-galactopyranoside, which produces a pink-red color upon cleavage, is chosen as the third substrate to which *E.coli* general coliforms and *Salmonella* are responsive.

In this example, *E. coli* colonies show as substantially black, general coliform colonies show as red-pink, and *Salmonella* show as blue-violet (=red-pink+teal).

Example XVI

The selected microorganisms to be detected, quantified and differentiated in this example are *E. coli* as a substantially black color and general coliforms as a second distinct color.

With reference to Table IV, *E. coli* produces the enzyme Bgluc, and Bgluc is not produced by any of the other microorganisms desired to be detected. Therefore, a substrate which produces a distinct color upon cleavage of Bgluc should be chosen from Table V. 8-hydroxyquinoline-β-D-glucuronide produces a dark color in the presence of Bgluc and would be the preferred choice of substrate. A metallic salt such as ferric ammonium citrate is also added to form a black water insoluble complex consisting of ferric ions and the aglycone released when the substrate is hydrolized by glucuronidase from *E. coli*.

With further reference to Table IV, Bgal, Bfuc and Bglu are common to *Aeromonas* and general coliforms. However, as indicated in Table IV, Bgal, Bfuc and Bglu are not generally produced by *Salmonella*. Therefore, a substrate can be selected from Table V which reacts with one of Bgal, Bfuc and Bglu to produce a second distinct color. 5-bromo-4-chloro-3-indolyl-β-D-galactopyranoside can be chosen as the second substrate, in which event colonies of *E. coli* will appear as substantially black and general coliform colonies will appear as teal. Optionally, 5-bromo-6-chloro-3-indolyl-galactopyranoside can be chosen as the second substrate, in which event colonies of *E. coli* will appear as substantially black and general coliform colonies will appear magenta. To avoid growth of *Aeromonas* colonies, an inhibitor, preferably nalidixic acid, is added. Thus, colonies of *E. coli* will show as substantially black, whereas colonies of general coliforms will show as a magenta color.

Example XVII

Some selected micro-organisms that can be detected, quantified and differentiated in this example are *E. coli*, general coliforms, *Aeromonas*, and/or *Salmonella*. The substrates 5-bromo-4-chloro-3-indolyl-β-D-glucuronide, 6-chloro-3-indolyl-β-D-galactopyranoside, and 5-bromo-4-chloro-3-indolyl-α-D-galactopyranoside are added in quantities of approximately 125 mg/l medium; 200 mg/l medium; and 65 mg/l medium, respectively. The remaining preparation and inoculation of the test medium in this example is similar to that discussed above, except that ions of salt are not required when the medium does not have a nonchromogenic substrate. In this medium, *E.coli*, which reacts with all of the substrates, will appear as a very dark blue and/or purple color because the high concentration of the β-D-glucuronide will predominate. The general coliforms, which react to both the α- and β-D-galactopyranoside appear as a light blue-gray color. *Salmonella*, which reacts with the α-D-galactopyranoside will have a teal color and *Aeromonas*, which reacts with β-D-galactopyranoside will have a pink-red color. It can be beneficial if the concentration/amount used of the β-D-glucuronide is greater than the β-D-galactopyranoside to increase the difference in coloration/darkness between the *E. coli* and general coliforms, since these substrates utilize the same color compound in this example. However, even if the same amounts of β-D-glucuronide and β-D-galactopyranoside are used, the *E. coli* may still be darker and distinguishable from general coliforms since it reacts to both of these substrates whereas the general coliforms do not react with the β-D-glucuronide.

Example XVIII

An alternate β-D-glucuronide substrate that may be utilized is 5-iodo-3-indolyl-β-D-glucuronide, which is commonly known as Iodo-Gluc. Selected micro-organisms to be detected, quantified and differentiated in this example are *E. coli*, general coliforms, *Aeromonas*, and *Salmonella*. The concentration of the β-D-glucuronide must be sufficient to provide a very dark purple color that can be readily distinguished from the blue-gray color of the general coliforms.

Example XIX

Another alternate β-D-glucuronide substrate that may be used is indoxyl-β-D-glucuronide, which is commonly known as IBDG. With a sufficient concentration of IBDG, *E. coli* will appear darker than the other colonies as a dark blue-purple color. General coliforms, *Salmonella*, and *Aeromonas* will appear as light blue-gray, teal and red-pink, respectively.

Example XX

In this example, 4-methylumbelliferyl-β-D-glucuronide, commonly known as MUGluc, is used instead of a chromogenic or nonchromogenic β-D-glucuronide. With this medium, *E. coli* will fluoresce under ultra-violet light, and general coliforms will be light blue-gray, *Salmonella* will be teal, and *Aeromonas* will be pink-red in ambient light. An advantage of the MUGluc is that the incubation times required for detection of the colonies may be substantially less than that required with the other chromogenic or nonchromogenic substrates. An incubation time of about 14 hours should be sufficient to detect *E. coli* with this substrate. A disadvantage is that the fluorescent products are more readily diffusible than the other compounds and may make it more difficult to quantify the *E. coli*. However, even if the *E. coli* can not be quantified in a given test, it will still certainly be suitable for a presence/absence test for *E. coli*.

Example XXI

In this medium, a 4-methylumbelliferyl-β-D-glucuronide (MUGluc) is combined with one of the other previously mentioned chromogenic or nonchromogenic glucuronide substrates as well as with chromogenic α- and β-D-galactopyranosides. This medium offers the advantage that a presence/absence test for *E. coli* may be performed with shorter incubation times than required for the chromogenic and nonchromogenic substrates. In addition, if for any reason, it is uncertain whether colonies of detected organisms are *E. coli* or general coliforms, the medium can be examined under ultra-violet light so that colonies of *E. coli* can be confirmed by fluorescence. This provides a double check on the accuracy of the identity of the colonies.

Although several broad examples which incorporate the present invention have been described above, it is to be understood that the present invention is not to be limited by the examples disclosed herein. Indeed, the disclosure and examples above teach one of ordinary skill a virtually limitless number of test media which would be within the scope of the claims appended hereto.

Further, while this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A test medium for detecting, quantifying or differentiating general coliforms, *E. coli, Aeromonas* spp. and *Salmonella* spp., said test medium comprising:
   a β-D-glucuronide substrate, which forms a first product in the presence of *E. coli;*
   an α-D-galactoside chromogenic substrate, which forms a second product in the presence of the *Salmonella*; and
   a β-D-galactoside chromogenic substrate, which forms a third product in the presence of *Aeromonas*, said products of said α-D-galactoside and said β-D-galactoside substrates combining to form a color in the presence of general coliforms, so that general coliforms, *E. coli, Aeromonas*, and *Salmonella* are distinguishable from one another.

2. The test medium of claim 1, wherein said β-D-glucuronide substrate and one of either said α-D-galactoside chromogenic substrate or said β-D-galactoside chromogenic substrate consist of the same color component, but in different amounts.

3. The test medium of claim 2, wherein said β-D-glucuronide substrate is 5-bromo-4-chloro-3-indolyl-β-D-glucuronide and said α-D-galactoside substrate is 5-bromo-4-chloro-3-indolyl-α-D-galactoside.

4. The test medium of claim 3, wherein said medium has a concentration of approximately 125 mg/l of β-D-glucuronide and 65 mg/l of α-D-galactoside.

5. The test medium of claim 1, wherein said β-D-glucuronide substrate is 5-iodo-3-indolyl-β-D-glucuronide.

6. The test medium of claim 1, wherein said β-D-glucuronide substrate is indoxyl-β-D-glucuronide.

7. The test medium of claim 1, wherein said first product, produced by said β-D-glucuronide substrate in the presence of *E. coli* fluoresces under ultra-violet light.

8. The test medium of claim 7, wherein said β-D-glucuronide substrate is 4-methylumbelliferyl-β-D-glucuronide.

9. The test medium of claim 7, further including a second β-D-glucuronide substrate, said second β-D-glucuronide substrate forming a product of color in the presence of *E. coli* that is detectable under ambient light and distinguishable from said first, second, and third products.

10. The test medium of claim 9, wherein said second β-D-glucuronide substrate is selected from the group consisting of 8-hydroxyquinoline-β-D-glucuronide, an esculetin glucuronide, cyclohexenoesculetin-β-D-glucuronide, 5-bromo-4-chloro-3-indolyl-β-D-glucuronide, 5-iodo-3-indolyl-β-D-glucuronide, and indoxyl-β-D-glucuronide.

* * * * *